(12) United States Patent
Lavik et al.

(10) Patent No.: US 8,492,334 B2
(45) Date of Patent: Jul. 23, 2013

(54) SUSTAINED INTRAOCULAR DELIVERY OF DRUGS FROM BIODEGRADABLE POLYMERIC MICROPARTICLES

(75) Inventors: Erin Lavik, Branford, CT (US); Young H. Kwon, Iowa City, IA (US); Markus Kuehn, Amana, IA (US); Sandeep Saluja, Fair Lawn, NJ (US); James Bertram, New Haven, CT (US); John Huang, Hamden, CT (US)

(73) Assignees: Yale University, New Haven, CT (US); University of Iowa Research Foundation, Iowa City, IA (US)

( * ) Notice: Subject to any disclaimer, the term of this patent is extended or adjusted under 35 U.S.C. 154(b) by 440 days.

(21) Appl. No.: 12/664,792

(22) PCT Filed: Jun. 18, 2008

(86) PCT No.: PCT/US2008/067362
§ 371 (c)(1),
(2), (4) Date: Jun. 18, 2010

(87) PCT Pub. No.: WO2008/157614
PCT Pub. Date: Dec. 24, 2008

(65) Prior Publication Data
US 2010/0261646 A1    Oct. 14, 2010

Related U.S. Application Data

(60) Provisional application No. 60/936,766, filed on Jun. 21, 2007, provisional application No. 61/051,224, filed on May 7, 2008.

(51) Int. Cl.
| | |
|---|---|
| *A61K 38/18* | (2006.01) |
| *A61K 38/22* | (2006.01) |
| *A61K 31/7036* | (2006.01) |
| *A61K 31/704* | (2006.01) |
| *A61K 31/57* | (2006.01) |
| *A61K 31/573* | (2006.01) |

(52) U.S. Cl.
USPC .............. 514/7.6; 514/9.7; 514/36; 514/37; 514/300

(58) Field of Classification Search
None
See application file for complete search history.

(56) References Cited

U.S. PATENT DOCUMENTS

| | | | |
|---|---|---|---|
| 3,266,987 A | 8/1966 | Crowley | |
| 4,460,563 A | 7/1984 | Calanchi | |
| 4,794,000 A | 12/1988 | Ecanow | |
| 5,731,005 A | 3/1998 | Ottoboni | |
| 5,766,242 A | 6/1998 | Wong | |
| 5,824,072 A | 10/1998 | Wong | |
| 5,837,226 A | 11/1998 | Jungherr | |
| 6,131,211 A | 10/2000 | Hennessey | |
| 6,235,224 B1 | 5/2001 | Mathiowitz | |
| 6,726,918 B1 | 4/2004 | Wong | |
| 2004/0234611 A1 | 11/2004 | Ahlheim | |
| 2005/0244458 A1 | 11/2005 | Huang | |
| 2005/0271705 A1* | 12/2005 | Hughes et al. | ................ 424/427 |
| 2006/0172972 A1 | 8/2006 | Bhushan | |
| 2006/0173060 A1 | 8/2006 | Chang | |
| 2006/0246145 A1 | 11/2006 | Chang | |
| 2008/0112923 A1 | 5/2008 | Hughes | |
| 2008/0118549 A1 | 5/2008 | Huang | |

FOREIGN PATENT DOCUMENTS

| | | |
|---|---|---|
| WO | 2005107706 | 11/2005 |
| WO | 2005107707 | 11/2005 |
| WO | 2005110424 | 11/2005 |

OTHER PUBLICATIONS

Abazinge, et al., "Comparison of In Vitro and In Vivo Release Characteristics of Sustained Release Ofloxacin Microspheres", Drug Delivery, 7:77-81 (2000).
Aggarwal, et al., "Improved Pharmacodynamics of Timolol Maleate from a Mucoadhesive Niosomal Ophthalmic Drug Delivery System", International J. of Pharmaceutics, 290(1-2):155-159 (2003).
Alward, et al., "The effectiveness of intraocular pressure reduction in the treatment of normal-tension glaucoma", Amer. J. Opthmal., 126(4):498-505 (1998).
Aniruddha, et al., "Single Periocular Injection of Celecoxib-PLGA Microparticles Inhibits Diabetes-Induced Elevations in Retinal PGE2, VEGF, and Vascular Leakage", Investigative Ophthalmology & Visual Science, 47(3):1149-1160 (2006).
Ansel, Pharmaceutical Dosage Forms and Drug Delivery Systems 6th Ed., Williams and Wilkins, 396-408 (1995).
Bloomdahl, et al., "Blindness in glaucoma patients", Acta. Opth. Scan., 75 (3):310-319 (1997).
Herrero-Vanrell, et al., "Biodegradable PLGA Microspheres Loaded with Ganciclovir Encapsulation Technique, in vitro Release Profiles, and Sterilization Process", Pharmaceutical Research, 17(10):1323-1328 (2000).

(Continued)

*Primary Examiner* — Julie Ha
(74) *Attorney, Agent, or Firm* — Pabst Patent Group LLP

(57) ABSTRACT

Biodegradable polymeric microparticle compositions containing one or more active agents, especially those useful for treating or preventing one or more diseases or disorders of the eye, and methods of making and using thereof, are described. In a preferred embodiment, the microparticle compositions contain one or more active agents useful for managing elevated intraocular pressure (IOP) in the eye. Relatively hydrophilic, and preferably carboxylated, polymeric materials such as PLGA are used for a drug such as timolol maleate, which is relatively water soluble, to increase drug loading. Higher molecular weight polymers, as well as the ratio of LA (which has a longer degradation time, up to one to two years) to GA (which has a short degradation time, as short as a few days to a week), are used to provide release over a longer period of time.

31 Claims, 8 Drawing Sheets

OTHER PUBLICATIONS

Li, et al., "Structure-property relationships in the case of the degradation of massive poly(±-hydroxy acids) in aqueous media", J. Mat. Sci.-Mat. Med., 1 (3):131-139 (1990).

Marquis and Whitson, "Management of glaucoma: focus on pharmacological therapy", Drugs & Aging, 22(1):1-21 (2005).

Migdal, et al., "Long-term functional outcome after early surgery compared with laser and medicine in open-angle glaucoma", Opthmal., 101(10):1651-1656 (1994).

Quigley, et al., "The number of people with glaucoma worldwide in 2010 and 2020", Brit. J. Opth., 90(3):262-267 (2006).

Rotchford and Murphy, "Compliance with timolol treatment in glaucoma.", Brit. J. Opthmal., 12(Pt 2):234-236 (1998).

Sato, et al., "Porous Biodegradable Microspheres for Controlled Drug Delivery. I. Assessment of Processing Conditions and Solvent Removal Techniques", Pharmaceutical Research, 5(1):21-30 (2005).

Schuman, "Antiglaucoma medications: a review of safety and tolerability issues related to their use.", Clin. Ther., 22(2):167-208 (2000).

Singh and Udupa, "In Vitro Characterization of Methotrexate Loaded Poly(lactic-co-glycolic) Acid Microspheres and Antitumor Efficacy in Sarcoma-180 Mice Bearing Tumor", Pharmaceutica Acta Helvetiae, 72:165-173 (1997).

"Timoptic-Xe", http://dailymed.hlm.nih.gov/dailymed/drugInfo.cfm?id=3153, (accessed Jun. 2, 2008).

Wu, et al., "Intravitreally Injectable Poly (D, L-Lactide) Microspheres Containing Dexamethasone Acetate for Sustained Release", Acta Pharmaceutica Sinica, 36 (10):766-770 (2001).

* cited by examiner

Figure 4a
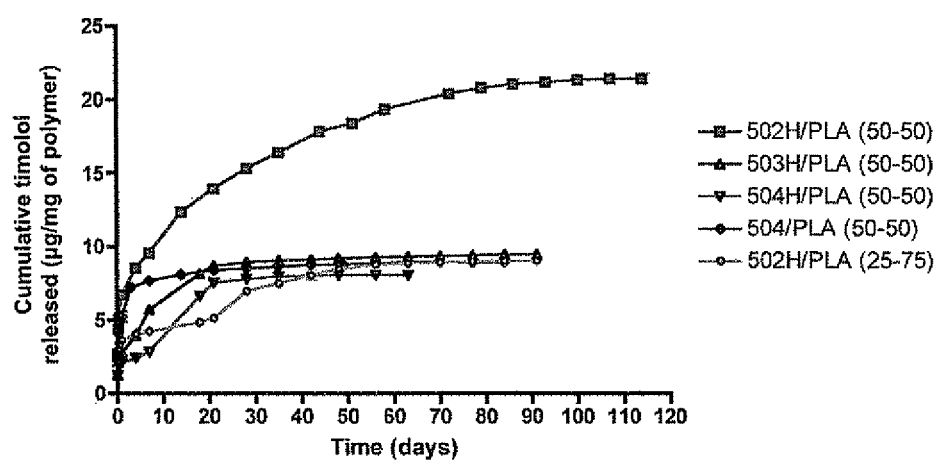
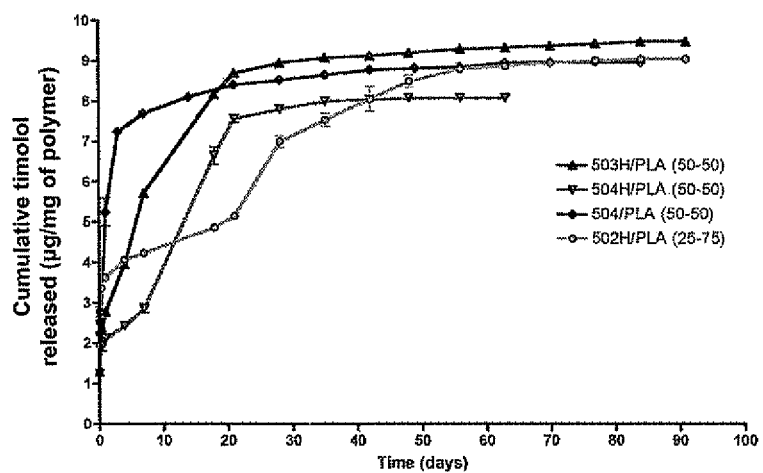
Figure 4b

RELEASE of OFLOXACIN LOADED PLGA MICROSPHERES

SUSTAINED INTRAOCULAR DELIVERY OF DRUGS FROM BIODEGRADABLE POLYMERIC MICROPARTICLES

CROSS-REFERENCE TO RELATED APPLICATIONS

This application is a filing under 35 U.S.C. 0371 of PCT/US2008/067362 filed with U.S. Receiving Office of the Patent Cooperation Treaty on Jun. 18, 2008, which claims priority to U.S. Ser. No. 60/936,766 entitled "Sustained Delivery of Timolol Maleate for the Management of Elevated Intraocular Pressure", filed on Jun. 21, 2007 and U.S. Ser. No. 61/051,224 entitled "Sustained Delivery of Timolol Maleate for the Management of Elevated Intraocular Pressure", filed on May 7, 2008. The disclosures in the applications listed above are herein incorporated by reference.

FIELD OF THE INVENTION

This invention is in the field of pharmaceutical compositions comprising biodegradable microparticles encapsulating high weight percent drug and providing sustained release over a prolonged period of time of drug levels bioequivalent to direct administration of drug.

BACKGROUND OF THE INVENTION

Polymeric microparticles have been used for drug delivery for decades. Numerous methods to increase the amount of drug which can be delivered, and to manipulate rate of release, and release profile, have been described. Methods have included altering microparticles size, shape, polymer composition, inclusion of additives such as surfactants and pore forming agents, and inclusion of ligands and bioadhesive agents.

Glaucoma is an ophthalmic disease characterized by the gradual degeneration of retinal ganglion cells (RGCs). RGCs synapse with bipolar cells and transmit visual inputs to the brain along the optic nerve. Degeneration of these cells leads to gradual vision loss and ultimately blindness if untreated. Glaucoma is the second leading cause of blindness (Biomdahl et al., *Acta. Opth. Scan.*, 75, 310-319 (1997)). Glaucoma will affect approximately 60.5 million people in 2010, increasing to 796 million people in 2020 (Quigley et al., *Brit. J. Opth.*, 90, 262-267 (2006)). This includes peoples suffering from both open angle (OAG) and angle closure glaucoma (ACG).

Although a normal tension variant does exist, the development of glaucoma is most often associated with elevated intraocular pressure (IOP) (Migdal et al., *Opthmal.*, 101, 1651-1656 (1994)). This elevated pressure is caused by an excess accumulation of aqueous humor in the eye due to blockage of the trabecular network (Alward et al., *Amer. J. Opthmal.*, 126, 498-505 (1998)). With a majority of glaucoma cases associated with elevated IOP, reduction of this pressure has been found to greatly mitigate degeneration in approximately 90% of the cases, including cases in which IOP is in the normal range but optic neuropathy occurs (Id).

Timolol maleate, a β-adrenergic receptor antagonist, induces an average IOP reduction of 20-35% when administered topically as a solution. Since its approval for ophthalmic applications in 1979, timolol maleate has become the FDA's gold standard for IOP reduction. Eye drops are currently the primary means of delivery for this drug. However, with less than 1% of the topically administered drug reaching the aqueous humor, large numbers of doses daily are required for IOP management. Compliance with this treatment regime is poor with more than half of patients unable to maintain consistently lowered IOP through drops (Rotchford and Murphy, *Brit. J. Opthmal.*, 12, 234-236 (1998)).

Drops also lead to extensive systemic absorption of the administered drug (~80%, Marquis and Whitson, *Drugs & Aging*, 22, 1-21 (2005)). This systemic absorption can result in adverse cardiopulmonary side effects (Schuman, *Clin. Ther.*, 22, 167-208 (2000)). Together, these complications make topical application of timolol maleate problematic, especially in the aging population that exhibits the lowest compliance and highest degree of complications (Marquis and Whitson, *Drugs & Aging*, 22, 1-21 (2005)). There exists a need for a sustained release timolol maleate formulation, which overcomes the limitations of currently available eye drops.

A variety of approaches for the sustained delivery of timolol maleate have been investigated, including the commercially available once daily gel-forming solutions (e.g., 0.5% Timoptic-XE® and Nyogel®), poly(D,L-lactice-co-glycolic acid) (PLGA) films, chitosan treated alginate beads, and soft contact lenses containing N,N-diethylacrylamide and methacrylic acid. None of the formulations, however, result in sustained release of timolol maleate for longer than 14 days, far short of the 90 day minimum delivery required to fundamentally alter the treatment of glaucoma. For example, Nyogel® (0.01% timolol hydrogel formulation) provides similar efficacy to 0.5% timolol aqueous solution eye drops with some reduction in side effects, but only lasts for 24 hours. PLGA films incorporating timolol maleate were studied, but release of the drug on the corneas of ocularly hypertensive rabbits was achieved for only five days. Further, few of these formulations are conducive to subconjunctival injection, a minimally invasive procedure well tolerated by patients, as they are formulated as contact lenses or plugs or films which are implanted on the eye. Such implants can be irritating to the eye and/or can fall out.

U.S. Pat. No. 6,726,918 to Wong describes methods for treating inflammation-mediated conditions of the eye, the methods including implanting into the vitreous of the eye a bioerodible implant containing a steroidal anti-inflammatory and a bioerodible polymer, wherein the implant delivers an agent to the vitreous in amount sufficient to reach a concentration equivalent to at least about 0.65 μg/ml dexamethasone within about 48 hours and maintains a concentration equivalent to at least about 0.03 μg/ml dexamethasone for at least about three weeks. Wong does not disclose administering the implants by subconjunctive injection.

U.S. Patent Application Publication No. 2006/0173060 to Chang et al. describes biocompatible microparticles containing an alpha-2-adrenergic receptor agonist and a biodegradable polymer. The microparticles can allegedly be used to treat glaucoma. Chang alleges that the microparticles release the active agent for a period of time of at least about one week, such as between two and six months. Chang discloses that the microparticles can be administered subconjunctivally.

U.S. Patent Application Publication No. 2004/0234611 to Ahlheim et al. describes an ophthalmic depot formulation containing an active agent embedded in a pharmacologically acceptable biocompatible polymer or a lipid encapsulating agent for periocular or subconjunctival administration. The formulation can be in the form of microparticles or nanoparticles. Ahlheim discloses that the depot formulations are adapted to release all or substantially all of the active material over an extended period of time (e.g., several weeks up to 6 months). Suitable active agents are listed in paragraphs 0033 to 0051 and include timolol maleate; however, the preferred active agent is a staurosporine, a phthalazine, or a pharmaceutically salt thereof. Suitable polymers are listed in paragraphs 0014 to 0026. Ahlheim does not show in vivo release of an effective amount of timolol maleate over a period of greater than 14 days. In fact, Ahlheim contains no examples showing in vitro or in vivo release of any active agents, let alone timolol maleate.

Aggarwal describes chitosan or Carbopol coated niosomal timolol maleate formulations prepared by reverse phase evaporation (REV) (Aggarwal et al., int. *J. Pharm., Vol.* 290 (1-2), 155-159 (2003)). The coated timolol maleate formulation was compared to timolol solution in term of in vitro release and IOP lowering pharmacodynamic effect. The coated timolol maleate formulations released 40-43% of the drug after 10 hours and showed a more sustained effect on IOP for up to eight hours. Aggarwal does not disclose or suggest release of an effective amount of timolol maleate over an extended period of time, for example, greater than 14 days.

None of the references discussed above optimizing the charge, hydrophilicity, an/or the molecular weight of the polymers used prepare microparticles in order to maximize drug loading and release of an effective amount of the drug for a desired period of time.

Therefore, it is an object of the invention to provide sustained release polymeric microparticulate compositions which have been optimized to maximize drug loading and release an effective amount of a drug (or drugs) for a desired period of time.

It is a further object of the present invention to provide such formulations useful for reducing intraocular pressure (IOP) which provide sustained release of an amount of drug comparable to that administered topically for more than 14 days in vivo, and methods of making and using thereof.

It is further an object of the invention to provide sustained release compositions of one or more active agents useful for reducing intraocular pressure (IOP) which provide sustained release for more than 14 days in vivo, and methods using thereof, wherein the compositions exhibit minimal adverse side effects and is well tolerated by patients.

SUMMARY OF THE INVENTION

Biodegradable polymeric microparticle compositions containing one or more water soluble active agents, especially those useful for treating or preventing one or more diseases or disorders of the eye, and methods of making and using thereof, are described. The microparticles are optimized for the drug to be delivered, so that the hydrophilicity and charge of the polymer maximizes loading of the drug, and the selection and molecular weight of the polymers maximize release of an effective amount of the drug for the desired period of time. The microsphere compositions release an effective amount of the one or more active agents for a period greater than 14 days in vivo, preferably greater than 60 days in vivo, more preferably up to 73 days in vivo, more preferably greater than 90 days in vivo, even more preferably over 100 days in vivo, and most preferably greater than 107 days in vivo. The desired amount and duration of release is dependent upon several factors including the disease or disorder to be treated, the one or more active agents to be delivered, and the frequency of administration.

In a preferred embodiment, the microparticle compositions contain one or more water soluble active agents useful for managing elevated intraocular pressure (IOP) in the eye. In one embodiment, the microspheres are formed from polylactide-co-glycolide ("PLGA"); in another embodiment, the microspheres are formed from a blend PLGA and polylactic acid ("PLA"). Relatively hydrophilic, and preferably carboxylated, polymeric materials such as PLGA are used for a drug such as timolol maleate, which is relatively water soluble, to increase drug loading. Higher molecular weight polymers, having different ratios of LA (which has a longer degradation time, up to one to two years) to GA (which has a short degradation time, as short as a few days to a week), are used to provide release over a longer period of time. The combination of drug loading and release rate, as well as the minimization of initial burst release, result in prolonged release of a higher amount of drug. As demonstrated by the examples, the microsphere compositions release timolol maleate for at least 90 days in an amount comparable to the amount provided by direct administration of a timolol maleate solution. Release for a period of 90 days or greater corresponds to the typical time period between ophthalmologist visits for patients suffering from glaucoma. The sustained release of drug, in combination with the ability to administer the drug in a minimally invasive manner, should increase patient compliance.

The microsphere compositions can be administered to the eye using a variety of techniques in the art. In one embodiment, the compositions are administered to the eye by injection. In a preferred embodiment, the microsphere composition is administered subconjunctivally. Subconjunctival administration is minimally invasive, and minimizes systemic absorption of the active agents.

BRIEF DESCRIPTION OF THE DRAWINGS

FIG. 2*a* shows the cumulative release of timolol maleate from PLGA 502H (□), PLGA 503H (Δ), PLGA 504H (∇), PLGA 504 (◇), PLGA 752 (○), and PLA (x) microspheres. FIG. 2*b* shows the cumulative release of timolol maleate from PLGA 502H (□), PLGA 503H (Δ), PLGA 504H (∇), PLGA 504 (◇), PLGA 752 (○), PLA (x), and microspheres prepared from a blend of PLGA:PLA (■).

FIG. 3*a* shows the cumulative timolol release from PLGA 502H(□), PLGA 503H (Δ), PLGA 504H (∇), PLGA 504 (◇), PLGA 752 (○) and PLA (x) microspheres. FIG. 3*b* shows the cumulative release of PLGA 502H (□), PLGA 503H (Δ), PLGA 504H (∇), PLGA 504 (◇), PLGA 752 (○), PLA (x), and microspheres prepared from a blend of PLGA:PLA (■).

FIGS. 4*a* and 4*b* are line graphs showing the in vitro cumulative release timolol maleate (μg of timolol maleate per mg of polymer) from microspheres prepared from various PLGA/PLA blends over time (days). FIG. 4*a* shows the in vivo release profiles were obtained for 502H/PLA (50-50) (■), 503H/PLA (50-50) (▲), 504H/PLA (50-50) (▼), 504/PLA (50-50) (♦), and 502H/PLA (25-75) (●) microspheres. FIG. 4*b* shows the in vivo release profiles for 503H/PLA (50-50) (▲), 504H/PLA (50-50) (▼), 504/PLA (50-50) (♦), and 502H/PLA (25-75) (●) microspheres.

DETAILED DESCRIPTION OF THE INVENTION

I. Definitions

Figure 1:
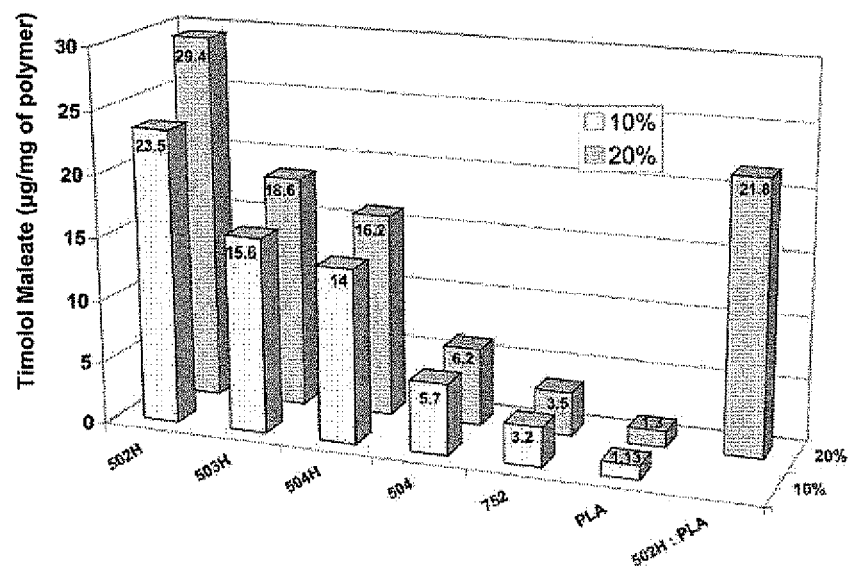
FIG. 1 is a bar graph showing the loading of timolol maleate (μg of drug/mg of polymer) as a function of polymer composition and molecular weight at 10% (light colored bars) and 20% (dark colored bars) timolol maleate concentration.

"Nanoparticle", as used herein, refers to particle or a structure in the nanometer (nm) range, typically from about 1 nm to about 1000 nm in diameter, which is encapsulated within the polymer.

"Microparticle", as used herein, generally refers to a particle of a relatively small size, but not necessarily in the micron size range; the term is used in reference to particles of sizes that can be, for example, administered to the eye subconjunctivally, and thus can be less than 50 nm to 100 microns or greater. In one embodiment, the diameter of the particles is from about 5 to about 25 microns, preferably from about 10 to about 25 microns, more preferably from about 10 to about 20 microns. As used herein, the microparticle encompasses microspheres, microcapsules and microparticles, unless specified otherwise. The relative sizes of microparticles and nanoparticles in the context of the present invention are such that the latter can be incorporated into the former. A micro- or nanoparticle may be of composite construction and is not necessarily a pure substance; it may be spherical or any other shape.

Formulations can be prepared using a pharmaceutically acceptable "carrier" composed of materials that are considered safe and effective and may be administered to an individual without causing undesirable biological side effects or unwanted interactions. As used herein, the "carrier" is all components present in the pharmaceutical formulation other than the active ingredient or ingredients. The term "carrier" includes, but is not limited to, solvents, suspending agents, dispersants, buffers, pH modifying agents, isotonicity modifying agents, preservatives, antimicrobial agents, and combinations thereof.

"Water-soluble drug", as used herein, refers to a drug having a solubility of greater than 10 mg/ml at 25° C., preferably greater than 25 mg/ml at 25° C., more preferably greater than 50 mg/ml at 25° C., most preferably greater than 100 mg/ml at 25° C.

"Hydrophilic polymer", as used herein, refers to polymers that have an affinity for water, though are not water soluble.

II. Compositions

A. Active Agents

The microparticle compositions described herein contain one or more water-soluble active agents, In one embodiment, the one or more active agents are useful for treating diseases or disorders of the eye. Suitable classes of active agents include, but are not limited to, active agents that lower intraocular pressure, antibiotics, chemotherapeutic agents, and steroids. Molecules which are not water-soluble can be chemically modified to make them water soluble, for example, by covalently attaching functional groups that increase the water-solubility of the drug without significantly affecting its efficacy. The active agents described above can be administered alone or in combination to treat diseases or disorders of the eyes.

Active Agents that Lower IOP

In one embodiment, the microparticles contain one or more active agents that manage (e.g., reduce) elevated IOP in the eye. In a preferred embodiment, the active agent is timolol or a pharmaceutically acceptable salt thereof, such as timolol maleate. Other suitable active agents include other beta-adrenergic receptor blockers, such as betaxolol, levobunolol, carteolol, and metipranolol; and combinations thereof. These active agents can be administered in place of timolol or in combination with timolol. The structures of these compounds are shown below:

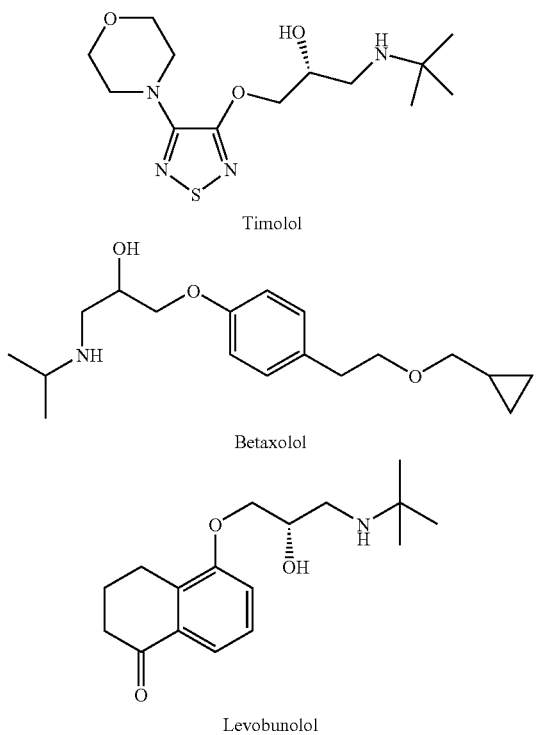

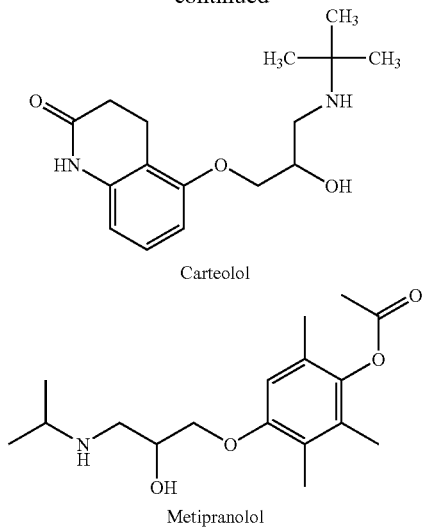

Carteolol

Metipranolol

Timolol maleate is a non-selective beta-adrenergic receptor blocker. In its oral form (Blocadren), it is used to treat high blood pressure and prevent heart attacks, and occasionally to prevent migraine headaches. In its ophthalmic form (brand names Timoptol in Italy; Timoptic), it is used to treat open-angle and occasionally secondary glaucoma by reducing aqueous humour production through blockade of the beta receptors on the ciliary epithelium. The pharmacological mechanism by which it actually does this is still unknown. For ophthalmic use, timolol can be combined with other medications: Cosopt® (timolol maleate and dorzolamide hydrochloride) and DuoTrav® (timolol and travoprost).

Betaxolol (trade names Betoptic®, Betoptic S®, Lokren®, Kerlone®) is a selective beta1 receptor blocker used in the treatment of hypertension and glaucoma. Being selective for beta1 receptors, it typically has fewer systemic side effects than non-selective beta-blockers, for example, not causing bronchospasm (mediated by beta2 receptors) such as timolol may. Betaxolol also shows greater affininty for beta1 receptors than metoprolol. In addition to its effect on the heart, betaxolol reduces the pressure within the eye (intraocular pressure). This effect is thought to be caused by reducing the production of the liquid (which is called the aqueous humor) within the eye. The precise mechanism of this effect is not known. The reduction in intraocular pressure reduces the risk of damage to the optic nerve and loss of vision in patients with elevated intraocular pressure due to eye diseases, such as glaucoma. Betaxolol was approved by the U.S. Food and Drug Administration (FDA) for ocular use as a 0.5% solution (Betoptic) in 1985 and as a 0.25% solution (Betoptic S) in 1989. Levobunolol, carteolol, and metpranolol are non-selective beta blockers that have been formulated in eye drops for the treatment of glaucoma.

Antibiotics

The microparticles compositions can contain one or more water soluble antibiotics. Suitable antibiotics include, but are not limited to, fluoroquinolone antibiotics, such as ofloxacin, levofloxacin, moxifloxacin, and gatifloxacin; aminoglycosides, such as streptomycin, kanamycin, aminodeoxykanamycin, kasugamycin, gentamicin, neomycin, tobramycin, netilmicin, and paromomycin; and diaminopyrimidines, such as trimethoprim.

Ofloxacin (sold under the brand name Floxin® in the United States, and Tarivid in Europe and some other countries) is a fluoroquinolone antibiotic. Ofloxacin is the racemic mixture of the chiral compound. The biologically active enantiomer is sold separately under the name of levofloxacin.

Growth Factors

In another embodiment, the water soluble active agent is a growth factor. Suitable growth factors include, but are not limited to, neurotrophic growth factors, such as brain-derived neurotrophic growth factor (BDNF), NT-3, and NT-4.

Brain-derived neurotrophic factor (BDNF) is a neurotrophic factor found in the brain and the periphery. It is a protein that acts on certain neurons of the central nervous system and the peripheral nervous system that helps to support the survival of existing neurons and encourage the growth and differentiation of new neurons and synapses. In the brain, it is active in the hippocampus, cortex, and basal forebrain—areas vital to learning, memory, and higher thinking.

Neurotrophins are chemicals that help to stimulate and control neurogenesis, BDNF being one of the most active. Mice born without the ability to produce BDNF suffer developmental defects in the brain and sensory nervous system, and usually die soon after birth, suggesting that BDNF plays an important role in normal neural development. Despite its name, BDNF is actually found in a range of tissue and cell types, not just in the brain. It is also expressed in the retina, the CNS, motor neurons, the kidneys, and the prostate.

BDNF has been used for a variety of neuroprotective applications as well as to reduce retinal damage caused by photodynamic therapy (PDT), such as choroidal neovascularization (CNV), a treatment for age-related macular degeneration.

NT-3 and NT-4 are neurotrophic factors, in the NGF (Nerve Growth Factor)-family of neurotrophins. They are protein growth factors which have activity on certain neurons of the peripheral and central nervous system; they help to support the survival and differentiation of existing neurons, and encourages the growth and differentiation of new neurons and synapses. The effects of axotomy and intraocular administration of NT-4, NT-3, and BDNF on the survival of adult rat retinal ganglion cells have been studied (*Investigative Opthalmology & Visual Science*, Vol 37, 489-500 (1996)). NT-4 and BDNF administered intraocularly at the time of axotomy exert a neuroprotective effect on axotomy-induced RGC death, thus increasing the population of surviving RGCs and delaying the onset of RGC of axotomy-induced RGC death by approximately 3 days. Intraocular administration of NT-3 did not modify the survival of RGCs after injury. This may have application in the treatment of glaucoma and other diseases or disorders of the eye.

Chemotherapeutic Agents and Steroids

The microparticle compositions can contain one or more water soluble chemotherapeutic agents and/or steroids, U.S. Pat. No. 7,214,710 to Crook et al. describes permeable, water soluble, non-irritating prodrugs of chemotherapeutic agents. Water insoluble chemotherapeutic agents can be covalently modified with mono- di- and polyoxaalkanoic or thiaalkanoic acids to increase the water-solublility of the chemotherapeutic agents and steroids. Crook describes the synthesis of water-soluble prodrugs of triamcinolone acetonide, AZT, DDI, DDC, acyclovir, ritonavir, saquinavir, gancyclovir, 5-fluorouracil, camptothecin, isoniazid. Other water soluble chemotherapeutic agents include, but are not limited to, edotides, which are water-soluble leaf extract of *Vernonia amygdalina*. Examples of water soluble steroids include, but are not limited to, hydroxydione, minaxolone, ORG 20599, and ORG 21465. These steroids are typically used as anaesthetics.

Pharmaceutically Acceptable Salts

The one or more active agents can be administered as the free acid or base or as a pharmaceutically acceptable acid addition or base addition salt.

Examples of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

B. Polymers

The microparticles described here can be formed from natural and/or synthetic polymeric materials. "Polymer" or "polymeric", as used herein, refers to oligomers, adducts, homopolymers, random copolymers, pseudo-copolymers, statistical copolymers, alternating copolymers, periodic copolymer, bipolymers, terpolymers, quaterpolymers, other forms of copolymers, substituted derivatives thereof, and combinations of two or more thereof (i.e., polymer blends). The polymers can be linear, branched, block, graft, monodisperse, polydisperse, regular, irregular, tactic, isotactic, syndiotactic, stereoregular, atactic, stereoblock, single-strand, double-strand, star, comb, dendritic, and/or ionomeric.

Bioerodible polymers may be used, so long as they are biocompatible. Preferred bio-erodible polymers are polyhydroxyacids such as polylactic acid and copolymers thereof. These are approved for implantation into humans.

Other suitable polymers have been described in great detail in the prior art. They include, but are not limited to: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate), poly vinyl chloride polystyrene and polyvinylpryrrolidone.

The bioerodable polymers may be used to provide delayed or extended release of nanoparticles comprising a diagnostic, therapeutic, or prophylactic agent.

As demonstrated by the examples, the percent loading is increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs. Alternatively, the polymer can be made more hydrophilic, for example, by introducing carboxyl groups onto the polymer. A combination of a hydrophilic drug and a hydrophobic drug can be encapsulated in microparticles prepared from a blend of a more hydrophilic PLGA and a hydrophobic polymer, such as PLA.

The percent loading of the one or more active agents in the microparticles is from about 1 to 50 weight percent, most preferably 5 to 30 weight percent, more preferably 10 to 20 weight percent.

The preferred polymer is a PLGA copolymer or a blend of PLGA and PLA. The molecular weight of PLGA is from about 10 kD to about 80 kD, more preferably from about 10 kD to about 35 kD. The molecular weight range of PLA is from about 20 to about 30 kDa. The ratio of lactide to glycolide is from about 75:25 to about 50:50. In one embodiment, the ratio is 50:50.

Exemplary polymers include, but are not limited to, poly (D,L-lactic-co-glycolic acid) (PLGA, 50:50 lactic acid to glycolic acid ratio, $M_n$ =10 kDa, referred to as 502H); poly (D,L-lactic-co-glycolic acid) (PLGA, 50:50 lactic acid to glycolic acid ratio, $M_n$=25 kDa, referred to as 503H); poly (D,L-lactic-co-glycolic acid) (PLGA, 50:50 lactic acid to glycolic acid ratio, $M_n$=30 kDa, referred to as 504H); poly (D,L-lactic-co-glycolic acid) (PLGA, 50:50 lactic acid to glycolic acid ratio, $M_n$=35 kDa, referred to as 504); and poly(D,L-lactic-co-glycolic acid) (PLGA, 75:25 lactic acid to glycolic acid ratio, $M_n$=10 kDa, referred to as 752).

The examples illustrate that loading is influenced by polymer molecular weight. Excluding PLGA 752, whose Mn and inherent viscosity (0.16-0.24 dl/g) are equivalent to that of PLGA 502H, timolol maleate loading was found to be inversely proportional to polymer molecular weight. Of the polymers with a 50:50 copolymer ratio, PLGA 502H had the greatest loading and PLGA 504 had the lowest loading. Comparing non-carboxylated PLGA (PLGA 504 and PLGA 752) and PLA, PLGA 504 loading was the highest (6.2 µg of timolol maleate per mg of microspheres), while PLGA 752 and PLA were the lowest, at 3.5 and 1.3 µg/mg respectively.

Comparing all polymers, loading was the lowest for PLGA 752. PLGA 752 was the most hydrophobic polymer tested and PLGA 502H was the most hydrophilic, indicating that loading decreases with polymer hydrophobicity for a hydrophilic drug, such as timolol maleate, which has a greater affinity for more hydrophilic polymers. Comparison of PLA, the most hydrophobic of the three polymers studied, with PLGA 504, the most hydrophilic polymer studied, supports this loading dependency on polymer hydrophilicity. Loading with PLGA 504 was approximately 5 times greater than PLA. Loading was also dependent on the presence of the carboxylic acid group, charge, and hydrophilicity. Loading with carboxylic acid containing PLGA 504H was approximately 2.5 times greater than that of its non-carboxyl terminated counterpart, PLGA 504. This is likely due to the presence of the carboxylic acid groups, which increase the hydrophilicity of the polymer.

The microsphere compositions described herein can release an effective amount of one or more active agents suitable for managing elevated IOP, such as timolol maleate, for a period greater than 14 days in vivo, preferably greater than 60 days in vivo, more preferably up to 73 days in vivo, more preferably greater than 90 days in vivo, even more preferably over 100 days in vivo, and most preferably greater than 107 days in vivo. Release for a period of 90 days or greater corresponds to the typical time period between ophthalmologist visits for patients suffering from glaucoma. The sustained release of drug, in combination with the ability to administer the drug in a minimally invasive manner, should increase patient compliance.

Excluding PLGA 752, it was observed that the length of timolol maleate release was directly proportional to the polymer molecular weight. While PLGA 502H had the greatest loading, it had the shortest release profile of approximately 10-15 days. PLGA 504 had the longest sustained release, approximately 35 days. Additionally, increasing the timolol maleate concentration from 10% to 20% induced a slight decrease in the rate of release.

The cumulative release profile for a hydrophobic polymer, such as PLGA 752, exhibited a substantial burst. Unlike other polymers whose release was approximately 10% over the first 3 hours, 43% of the timolol maleate was released from PLGA 752 in the first 3 hours. This burst was followed by a delay in release until day 38 and subsequent sustained delivery up to day 73, at which point no microspheres remained. The more hydrophobic polymers (PLGA 752 and PLA) exhibited substantial bursts at early time points (within the first day), followed by a small or delayed release over prolonged periods of time (56-73 days). The initial burst of timolol maleate released from PLGA 752 and PLA can be attributed to the relative hydrophobicity of the polymers. Due to timolol maleate's hydrophilic nature, the drug's affinity for the hydrophilic polymers will be greater. Therefore, a lack of association with a more hydrophobic polymer (e.g., PLGA 752 or PLA) may lead to, when exposed to aqueous conditions, an increased leaching of the drug from the microspheres is observed. With respect to PLGA 752, the delayed release (38-73 days) correlates with a slower rate of microsphere degradation. This delayed rate if degradation is due to the polymer's relative hydrophobicity. This reasoning also supports the observation that while PLA microspheres were present for approximately 100 days, the release of timolol maleate lasted no longer than 56 days.

PLGA microspheres with carboxyl end groups had the shortest release profiles of 14-21 days. Previous studies have shown an accelerated degradation rate of PLGA devices due to polymer carboxyl end groups (Li et al., *J. Mat. Sci.-Mat. Med.*, 1, 131-139 (1990)) as seen with the shorter release profiles of PLGA 502H, 503H, and 504H. This carboxyl end group influence is noticeable when comparing the release of PLGA 504H and PLGA 504. Even with equivalent molecular weights, the release of timolol maleate from PLGA 504 is sustained 14 days longer than PLGA 504H, 35 and 21 days, respectively. The release of timolol maleate was found to correlate with the rates of polymer degradation. The lower molecular weight PLGA 502H has more carboxylic acid end groups and therefore a faster rate of degradation In one embodiment, the microparticles are formed from poly(D,L-lactice-co-glycolic acid (PLGA, 50:50 lactic acid to glycolic acid ratio, $M_n$=10 kDa, referred to as 502H). In another embodiment, the microparticles are formed from poly(D,L-lactice-co-glycolic acid (PLGA, 50:50 lactic acid to glycolic acid ratio, $M_n$=25 kDa, referred to as 503H). In still another embodiment, the microparticles are formed from poly(D,L-lactice-co-glycolic acid (PLGA, 50:50 lactic acid to glycolic acid ratio, $M_n$=30 kDa, referred to as 504H). In yet another embodiment, the microparticles are formed from poly(D,L-lactice-co-glycolic acid (PLGA, 50:50 lactic acid to glycolic acid ratio, $M_n$=35 kDa, referred to as 504). In still another embodiment, the microparticles are formed from poly(D,L-lactice-co-glycolic acid (PLGA, 75:25 lactic acid to glycolic acid ratio, $M_n$=10 kDa, referred to as 752). In yet another embodiment, the microparticles are prepared from a blend of PLGA and PL (referred to as PLGA:PL). The designation "H" means the polymer is terminated with a carboxylic acid group. Microparticles can also be prepared from polylactic acid. As demonstrated by the examples, the H polymers are preferred for loading of hydrophilic drug.

C. Solvents and Surfactants for Preparation of Microparticles

Typical solvents are organic solvents such as methylene chloride, which leave low levels of residue that are generally accepted as safe. Suitable water-insoluble solvents include methylene chloride, chloroform, carbon tetrachloride, dicholorethane, ethyl acetate and cyclohexane. Additional solvents include, but are not limited to, alcohols such as methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1-ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, Di(ethylene glycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-pentanediol, 3,5-pentanediol, and combinations thereof.

D. Excipients for Administration to the Eye

Considerations in the formulation of the microsphere compositions include, but are not limited to, sterility, preservation, isotonicity, and buffering. The preparation of ophthalmic solutions and suspensions are described in Ansel et al., *Pharmaceutical Dosage Forms and Drug Delivery Systems* 6$^{th}$ Ed., pp. 396-408, Williams and Wilkins (1995). Suspensions are often more advantageous than solution as they typically have increased corneal contact time and thus can provide higher efficacy. Ophthalmic suspensions must contain particles of appropriate chemical characteristics and size to be non-irritating to the eyes. The suspension must also not agglomerate upon administration. Excipients, such as dispersants, can be included to prevent aggregation of the particles.

The microspheres are typically suspended in sterile saline, phosphate buffered saline, or other pharmaceutically acceptable carriers for administration to the eye.

Materials that may be used to formulate or prepare the microparticles include anionic, cationic, amphoteric, and non-ionic surfactants. Anionic surfactants include di-(2 ethylhexyl) sodium sulfosuccinate; non-ionic surfactants include the fatty acids and the esters thereof; surfactants in the amphoteric group include (1) substances classified as simple, conjugated and derived proteins such as the albumins, gelatins, and glycoproteins, and (2) substances contained within the phospholipid classification, for example lecithin. The amine salts and the quaternary ammonium salts within the cationic group also comprise useful surfactants. Other surfactant compounds useful to form coacervates include polysaccharides and their derivatives, the mucopolysaccharides and the polysorbates and their derivatives. Synthetic polymers that may be used as surfactants include compositions such as polyethylene glycol and polypropylene glycol. Further examples of suitable compounds that may be utilized to prepare coacervate systems include glycoproteins, glycolipids, galactose, gelatins, modified fluid gelatins and galacturonic acid.

Hydrophobic surfactants such as fatty acids and cholesterol are added during processes to improve the resulting distribution of hydrophobic drugs in hydrophobic polymeric microparticles. Examples of fatty acids include butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid and arachidonic acid.

In one embodiment, the surfactant polyvinyl alcohol is used to prepare the microparticles. Studies indicate that percent loading is dependent on the nature of surfactant used in the double emulsion methods described above. For example, using the PLGA/PLA blend and 20% timolol maleate by weight, a loading of 18.76 µg of timolol/mg of spheres was obtained when a 5% PVA solution was used. In contrast, the load of timolol was 2.3 µg per mg of spheres when the spheres were prepared using a 5% poly(ethylene-alt-maleic anhydride) (PEMA) solution.

III. Methods of Making

There are several processes whereby microparticles can be made, including, but not limited to, spray drying, interfacial polymerization, hot melt encapsulation, phase separation encapsulation, spontaneous emulsion, solvent evaporation microencapsulation, solvent removal microencapsulation, coacervation, low temperature microsphere formation, and phase inversion nanoencapsulation ("PIN").

The dispersion of the one or more active agents within the polymer matrix can be enhanced by varying: (1) the solvent used to solvate the polymer; (2) the ratio of the polymer to the solvent; (3) the particle size of the material to be encapsulated; (4) the percentage of the active agent(s) relative to the polymer (e.g., drug loading); and/or the polymer concentration.

The following are representative methods for forming microparticles.

Spray Drying

In spray drying, the core material to be encapsulated is dispersed or dissolved in a solution. Typically, the solution is aqueous and preferably the solution includes a polymer. The solution or dispersion is pumped through a micronizing nozzle driven by a flow of compressed gas, and the resulting aerosol is suspended in a heated cyclone of air, allowing the solvent to evaporate from the microdroplets. The solidified microparticles pass into a second chamber and are trapped in a collection flask.

Interfacial Polycondensation

Interfacial polycondensation is used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

Hot Melt Encapsulation

In hot melt microencapsulation, the core material (to be encapsulated) is added to molten polymer. This mixture is suspended as molten droplets in a nonsolvent for the polymer (often oil-based) which has been heated to approximately 10° C. above the melting point of the polymer. The emulsion is maintained through vigorous stirring while the nonsolvent bath is quickly cooled below the glass transition of the polymer, causing the molten droplets to solidify and entrap the core material.

Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid microcapsules containing core material.

The solvent evaporation process can be used to entrap a liquid core material in a polymer such as PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a microcapsule composed of polymer or copolymer shell with a core of liquid material.

Solvent evaporation microencapsulation can result in the stabilization of insoluble drug particles in a polymeric solution for a period of time ranging from 0.5 hours to several months.

The stabilization of insoluble drug particles within the polymeric solution could be critical during scale-up. By stabilizing suspended drug particles within the dispersed phase, said particles can remain homogeneously dispersed throughout the polymeric solution as well as the resulting polymer matrix that forms during the process of microencapsulation. The homogeneous distribution of drug particles can be achieved in any kind of device, including microparticles, nanoparticles, rods, films, and other device.

Solvent evaporation microencapsulation (SEM) has several advantages. SEM allows for the determination of the best polymer-solvent-insoluble particle mixture that will aid in the formation of a homogeneous suspension that can be used to encapsulate the particles. SEM stabilizes the insoluble particles or within the polymeric solution, which will help during scale-up because one will be able to let suspensions of insoluble particles sit for long periods of time, making the process less time-dependent and less labor intensive. SEM allows for the encapsulated particles to remain suspended within a polymeric solution for up to 30 days, which may increase the amount of insoluble material entrapped within the polymeric matrix, potentially improving the physical properties of the drug delivery vehicle. SEM allows for the creation of microparticles or nanoparticles that have a more optimized release of the encapsulated material. For example, if the insoluble particle is localized to the surface of the microparticle or nanoparticle, the system will have a large 'burst' effect. In contrast, creating a homogeneous dispersion of the insoluble particle within the polymeric matrix will help to create a system with release kinetics that begin to approach the classical 'zero-ordered' release kinetics that are often perceived as being ideal in the field of drug delivery).

Solvent Removal Micro Encapsulation

In solvent removal microencapsulation, the polymer is typically dissolved in an oil miscible organic solvent and the material to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

Coacervation

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.).

Through the process of coacervation compositions comprised of two or more phases and known as coacervates may be produced. The ingredients that comprise the two phase coacervate system are present in both phases; however, the colloid rich phase has a greater concentration of the components than the colloid poor phase.

Phase Inversion Nanoencapsulation ("PIN")

A preferred process is PIN. In PIN, a polymer is dissolved in an effective amount of a solvent. The agent to be encapsulated is also dissolved or dispersed in the effective amount of the solvent. The polymer, the agent and the solvent together form a mixture having a continuous phase, wherein the solvent is the continuous phase. The mixture is introduced into an effective amount of a nonsolvent to cause the spontaneous formation of the microencapsulated product, wherein the solvent and the nonsolvent are miscible. PIN has been described by Mathiowitz et al. in U.S. Pat. Nos. 6,131,211 and 6,235,224. A hydrophobic agent is dissolved in an effective amount of a first solvent that is free of polymer. The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less.

An improved process is demonstrated in the examples. The process uses a mixed solvent including at least one water-insoluble solvent and water that contains a surfactant, such as PVA. The drug is either dissolved or dispersed together with a substance that has a high molecular weight (such as a polymer) into an organic solvent composition, optionally containing non-ionic surfactants of various hydrophilic-lipophilic ratios. The composition is then introduced into an aqueous solution that contains a surfactant like PVA. The water-insoluble solvent forms an oil phase (inner phase) and is stirred into the aqueous solution as a water phase (outer phase). The O/W emulsion is combined with fresh water that contains surfactant such as PVA and is stirred to help aid the solvent evaporation. The aqueous solution contains an activator such as polyvinyl alcohol, whereby the oil phase is enclosed as small droplets within the aqueous solution as shells. The proportion of the water-miscible solvent in the oil phase is from 5% to 95%. An important aspect of this improved method is the use of high shear during the initial mixing phase, which is achievable, for example, using sonication for a period of one hour, with stirring, to uniformly mix in high amounts of drug particles in the polymer liquefied by dissolution or by melting.

Melt-Solvent Evaporation Method

In the melt-solvent evaporation method, the polymer is heated to a point of sufficient fluidity to allow ease of manipulation (for example, stirring with a spatula). The temperature required to do this is dependent on the intrinsic properties of the polymer. For example, for crystalline polymers, the temperature will be above the melting point of the polymer. After reaching the desired temperature, the agent is added to the molten polymer and physically mixed while maintaining the temperature. The molten polymer and agent are mixed until the mixture reaches the maximum level of homogeneity for that particular system. The mixture is allowed to cool to room temperature and harden. This may result in melting of the agent in the polymer and/or dispersion of the agent in the polymer. This can result in an increase in solubility of the drug when the mixture is dissolved in organic solvent. The process is easy to scale up since it occurs prior to encapsulation. High shear turbines may be used to stir the dispersion, complemented by gradual addition of the agent into the polymer solution until the desired high loading is achieved. Alternatively the density of the polymer solution may be adjusted to prevent agent settling during stirring.

This method increases microparticle loading as well as uniformity of the resulting microparticles and of the agent within the microparticles. When an agent is formed into microspheres by double-emulsion solvent evaporation, transfer of the agent from the inner phase to the outer water phase can be prevented. This makes it possible to increase the percentage of agent entrapped within the microspheres, resulting in an increased amount of the drug in the microspheres.

The distribution of the agent in particles can also be made more uniform. This can improve the release kinetics of the agent. Generally, the agent is dissolved or dispersed together with a substance that has a high molecular weight in an organic solvent composition; with or without non-ionic surfactants of various hydrophilic-lipophilic ratios. The composition is introduced into an aqueous solution that contains a surfactant like PVA. The water-insoluble solvent forms an oil phase (inner phase) and is stirred into the aqueous solution as a water phase (outer phase). The O/W emulsion is combined with fresh water that contains PVA and is stirred to help aid the solvent evaporation. The aqueous solution contains an activator such as polyvinyl alcohol, whereby the oil phase is enclosed as small droplets within the aqueous solution as shells.

In one embodiment, the microparticles are formed using a water-in-oil double emulsion (w/o/w) solvent evaporation technique. For example, the one or more active agents are dissolved in deionized water. The polymer is dissolved in an organic solvent or cosolvent. The aqueous and organic phases are emulsified via vortexing to obtain the desired active agent to polymer ratio (e.g., 10%, 20%, or greater). The emulsion is then added dropwise to an aqueous solution of a surfactant (such as polyvinyl alcohol) and allowed to stir/harden for 3 hours. The resulting microparticles are collected, such as by centrifugation, washed with deionized water, and dried (e.g., freeze drying). As demonstrated by the examples, the percent loading is increased by "matching" the hydrophilicity or hydrophobicity of the polymer to the agent to be encapsulated. In some cases, such as PLGA, this can be achieved by selecting the monomer ratios so that the copolymer is more hydrophilic. Alternatively, the polymer can be made more hydrophilic, for example, by treating the polymer with a carboxyl solution.

The percent loading of the one or more active agents in the microparticles is from about 1 to about 50 wt %, preferably from about 1 to about 20 wt %, more preferably from about 10 to about 20 wt %. In one embodiment, the percent loading of the drug is 10 wt % or 20 wt %. As demonstrated by the examples, the percent loading is increased by "matching" the hydrophilicity of the polymer to the water soluble agent to be encapsulated. Alternatively, the polymer can be made more hydrophilic, for example, by introducing carboxyl groups on to the polymer. A combination of a hydrophilic drug and a hydrophobic drug can be encapsulated in microparticles prepared from a blend of a more hydrophilic PLGA and a hydrophobic polymer, such as PLA.

IV. Methods of Use

A. Disorders to be Treated

The microsphere compositions described herein can be administered to treat or prevent diseases or disorders, most preferably of the eye. The dosage of the drug which is released at the site of administration should be bioequivalent as defined by the Food and Drug Administration for the drug when administered in solution, suspension or enterally, in the absence of the microparticles.

Glaucoma

In one embodiment, the microsphere compositions can be administered to manage (e.g., reduce) IOP in patients needing such treatment, for example, patients suffering from glaucoma. Glaucoma is an ophthalmic disease characterized by the gradual degeneration of retinal ganglion cells (RGCs). RGCs synapse with bipolar cells and transmit visual inputs to the brain along the optic nerve. Degeneration of these cells leads to gradual vision loss and ultimately blindness if untreated. Administration of timolol maleate, betaxolol, levobunolol, carteolol, metipranolol or combinations thereof are expected to lower IOP in patients needing such treatment.

Uveitis

Uveitis specifically refers to inflammation of the middle layer of the eye, termed the "uvea" but in common usage may refer to any inflammatory process involving the interior of the eye. Uveitis is estimated to be responsible for approximately 10% of the blindness in the United States. Uveitis requires an urgent referral and thorough examination by an ophthalmologist, along with urgent treatment to control the inflammation.

Uveitis is usually categorized anatomically into anterior, intermediate, posterior and panuveitic forms. Anywhere from two-thirds to 90% of uveitis cases are anterior in location (anterior uveitis), frequently termed iritis—or inflammation of the iris and anterior chamber. This condition can occur as a single episode and subside with proper treatment or may take on a recurrent or chronic nature. Symptoms include red eye, injected conjunctiva, pain and decreased vision. Signs include dilated ciliary vessels, presence of cells and flare in the anterior chamber, and keratic precipitates ("KP") on the posterior surface of the cornea. Intermediate uveitis consists of vitritis—inflammatory cells in the vitreous cavity, sometimes with snowbanking, or deposition of inflammatory material on the pars plana. Posterior uveitis is the inflammation of the retina and choroid. Pan-uveitis is the inflammation of all the layers of the uvea.

Myriad conditions can lead to the development of uveitis, including systemic diseases as well as syndromes confined to the eye. In anterior uveitis, no specific diagnosis is made in approximately one-half of cases. However, anterior uveitis is often one of the syndromes associated with HLA-B27.

The prognosis is generally good for those who receive prompt diagnosis and treatment, but serious complication (including cataracts, glaucoma, band keratopathy, retinal edema and permanent vision loss) may result if left untreated. The type of uveitis, as well as its severity, duration, and responsiveness to treatment or any associated illnesses, all factor in to the long term prognosis. Uveitis can be treated using steroids, such as prednisolone, and chemotherapeutic agents, such as methotrexate. In a preferred embodiment, the microspheres are loaded with ofloxacin, prednisolone, or a combination thereof. The microspheres preferably provide release of the one or more active agents for a period of between 14 and 21 days. In another embodiment, the microspheres provide sustained release of the one or more active agents over a period greater than three weeks, preferably over a period of greater than 49 days, more preferably over a period of two months, most preferably over a period of three months.

Post Surgical Ocular Inflammation/Infection

Most surgeries involving the eye are followed by ocular inflammation and/or infection. Topical administration of eye drops containing a combination of a steroid and an antibiotic is the predominant treatment for controlling inflammation as well as infection. Although such eye drops have been shown to be effective, poor compliance and the risk of re-opening of the stitched wound due to continuous touching of the wound when applying the eye drops remain fundamental issues. Therefore, it is desirable to provide a long-term ocular delivery system that provides release of the active agents for approximately 2-3 weeks in order to minimize dosing frequency, improve patient compliance, reduce side effects due to systemic absorption of the active agents, and keep the stitched wound intact. In one embodiment, microspheres loaded with an antibiotic, a steroid, or combinations thereof are administered to a patient post eye surgery. In a preferred embodiment, the microspheres are loaded with ofloxacin, prednisolone, or a combination thereof. The microspheres preferably provide release of the one or more active agents for a period of between 14 and 21 days. In another embodiment, the microspheres provide sustained release of the one or more active agents over a period greater than three weeks, preferably over a period of greater than 49 days, more preferably over a period of two months, most preferably over a period of three months.

Dry Eye Syndrome

Dry eye syndrome (Keratoconjunctivitis sicca (KCS)) is one of the most common problems treated by eye physicians. Over ten million Americans suffer from dry eyes. It is usually caused by a problem with the quality of the tear film that lubricates the eyes.

Dry eye syndrome has many causes. One of the most common reasons for dryness is simply the normal aging process. As we grow older, our bodies produce less oil—60% less at age 65 then at age 18. This is more pronounced in women, who tend to have drier skin then men. The oil deficiency also affects the tear film. Without as much oil to seal the watery layer, the tear film evaporates much faster, leaving dry areas on the cornea.

Many other factors, such as hot, dry or windy climates, high altitudes, air-conditioning and cigarette smoke also cause dry eyes. Contact lens wearers may also suffer from dryness because the contacts absorb the tear film, causing proteins to form on the surface of the lens. Certain medications, thyroid conditions, vitamin A deficiency, and diseases such as Parkinson's and Sjogren's can also cause dryness.

Inflammation occurring in response to tears film hypertonicity can be treated by administering the microspheres described herein loaded with water soluble steroids and/or with water soluble immunosuppressants.

Macular Degeneration

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. According to the American Academy of Opthalmology, it is the leading cause of central vision loss (blindness) in the United States today for those over the age of fifty years. Although some macular dystrophies that affect younger individuals are sometimes referred to as macular degeneration, the term generally refers to age-related macular degeneration (AMD or ARMD). Macular degeneration can be treated using anti-angiogenesis inhibitors. In one embodiment, the microspheres are loaded with a water-soluble anti-angiogenesis inhibitor or growth factor for the treatment of macular degeneration.

B. Methods of Administration

The composition can be administered using a variety of techniques well known in the art including, but not limited to, topically and by injection. Suitable dosage forms include but are not limited to, ointments and solutions and suspensions, such as eye drops. In one embodiment, the compositions are administered to the eye by injection. In a preferred embodiment, the microsphere composition is administered subconjunctivally. "Subconjunctival" or "subconjunctivally", as used herein, refers to administration under the white (i.e., conjunctiva) of the eye. The conjunctiva is the clear membrane that coats the inner aspect of the eyelids and the outer surface of the eye. The microsphere compositions are generally administered as suspensions in a pharmaceutically acceptable carrier, such as phosphate buffered saline (PBS). Subconjunctival administration of drugs, typically by injection, has shown minimal concentration of drug in the plasma and notable concentrations in the eye, including the aqueous humor.

Timolol maleate, a β-adrenergic receptor antagonist, induces an average IOP reduction of 20-35%. Eye drops are currently the primary means of delivery for this drug. Upon administration to the eye, approximately 80% passes through the nasolacrimal canal and is systemically absorbed and less than 1% of the topically administered drug reaching the aqueous humor. This systemic absorption is associated with adverse cardiopulmonary side effects, which is exacerbated by the need for frequent high doses to achieve controlled IOP. Together, these complications make topical application of timolol maleate problematic, especially in the aging population that exhibits the lowest compliance and highest degree of complications (Marquis and Whitson, *Drugs & Aging*, 22, 1-21 (2005)).

V. Kits

The kits contain the microsphere compositions and optionally one or more pharmaceutically acceptable excipients or carriers. In one embodiment, the kit can contain the microspheres in dry powder form in one container, such as a vial, jar, or ampule, and the pharmaceutically acceptable carrier in another container, such as a vial, jar, or ampule. The kit typically would contain instructions for resuspending the microparticles in the carrier and for administering the composition. If excipients are present, they can be in one or both containers.

In another embodiment, the kit can contain the microparticles resuspended in the carrier and optionally one or more pharmaceutically excipients. The kit would typically contain instructions for administering the composition. The kit can also contain one or more apparatus for preparing and/or administering the compositions, such as a needle and syringe. The container(s) containing the microspheres and the carrier can be packaged using techniques well known in the art. Suitable package materials include, but are not limited to, boxes Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Materials poly(D,L-lactic-co-glycolic acid (PLGA, 50:50 lactic acid to glycolic acid ratio, $M_n$=10 kDa, referred to as 502H);

poly(D,L-lactic-co-glycolic acid (PLGA, 50:50 lactic acid to glycolic acid ratio, $M_n$=25 kDa, referred to as 503H); poly(D,L-lactic-co-glycolic acid (PLGA, 50:50 lactic acid to glycolic acid ratio, $M_n$=30 kDa, referred to as 504H); poly(D,L-lactic-co-glycolic acid (PLGA, 50:50 lactic acid to glycolic acid ratio, $M_n$, =35 kDa, referred to as 504); and poly(D,L-lactic-co-glycolic acid (PLGA, 75:25 lactic acid to glycolic acid ratio, $M_n$=10 kDa, referred to as 752) were purchased from Boehringer Ingelheim (Ingelheim, Germany). The designation "H" means the polymer is terminated with a carboxylic acid group.

Poly(D,L-lactic acid) (PLA, $M_n$=~20-30 kDa) and poly(vinyl alcohol) (PVA, 88 mol % hydrolyzed) were purchased from Polyscienes (Warrington, Pa., USA).

Timolol maleate was purchased from Sigma (St. Louis, Mo., USA).

All other chemicals were A.C.S. reagent grade from Sigma (St. Louis, Mo., USA).

Example 1

Preparation of Microspheres

A water-in-oil-in-water (w/o/w) double emulsion solvent evaporation technique was used for microsphere fabrication. 20 or 40 mg of timolol maleate was dissolved in 300 µl of deionized water. 200 mg of polymer (or polymer blend, such as 50:50 blend of PLGA 502H and PLA) was dissolved in 1 ml of dichloromethane and 4 ml of trifluoroethanol. The aqueous and organic phases were emulsified via vortexing to obtain a desired drug polymer ratio of 10% or 20%. The emulsion was added dropwise to 200 ml of 5% (w/v) PVA aqueous solution and allowed to stir/harden for 3 hours. The microspheres were collected by centrifugation, washed three times with deionized water, and freeze dried for 3 days. Blank microspheres were made at the same time under identical conditions except that no timolol maleate was added.

Timolol Maleate Microsphere Loading

To determine the loading of timolol maleate, 5 mg of timolol maleate-containing microspheres or blank microspheres were placed in a glass scintillation vial with a screw cap. One milliliter of 1 N NaOH was added to the sample and the mixture was incubated at 37° C. for 2 days to allow complete digestion of the microspheres. After 2 days, 1 ml of 1 N HCl solution and 1 ml of deionized water was added to the tube. The timolol content in the solution of digested spheres was determined using a Cary 50 ultraviolet (UV) spectrophotometer (Varian, Inc.) at 293 nm. Plotting UV absorbance versus timolol maleate concentration produced a calibration curve for quantification of timolol maleate. A linear fit was established from ~0.6-80 µg/ml of timolol maleate in PBS (Y=0.0186x+0.0032; $r^2$=0.9998). Loading and release characteristics of the microspheres were determined using this calibration curve. The results are shown in FIG. 1.

Microspheres fabricated with a 20% timolol maleate concentration resulted in consistently higher loading than those with a 10% concentration. Based on these results and the goal of maximizing timolol maleate content, only a 20% concentration was studied in the blended polymer microsphere formulations.

Comparing PLGA microspheres alone, loading was influenced by polymer molecular weight. Excluding PLGA 752, whose Mn and inherent viscosity (0.16-0.24 dl/g) are equivalent to that of PLGA 502H, timolol maleate loading was found to be inversely proportional to polymer molecular weight. Of the polymer with a 50:50 copolymer ratio, PLGA 502H had the greatest loading and PLGA 504 had the lowest loading. Comparing non-carboxylated PLGA (PLGA 504 and PLGA 752) and PLA, PLGA 504 loading was the highest (6.2 µg of timolol maleate per mg of microspheres), while PLGA 752 and PLA were the lowest, at 3.5 and 1.3 µg/mg respectively.

Comparing all polymers, loading was the lowest for PLGA 752. PLGA 752 was the most hydrophobic polymer tested and PLGA 502H was the most hydrophilic, suggesting that loading decreases with polymer hydrophobicity. This is to be expected for a hydrophilic drug, such as timolol maleate, Comparison of PLA, the most hydrophobic of the three polymers studied, with PLGA 504, the most hydrophilic polymer studied, supports this loading dependency on polymer hydrophilicity. Loading with PLGA 504 was approximately 5 times greater than PLA.

Loading was also dependent on the presence of the carboxylic acid group, charge, and hydrophilicity. Loading with carboxylic acid containing PLGA 504H was approximately 2.5 times greater than that of its non-carboxyl terminated counterpart, PLGA 504.

Finally, loading was dependent on the surfactant used in the double emulsion methods described above. Using the PLGA/PLA blend and 20% timolol maleate by weight, a loading of 18.76 µg of timolol/mg of spheres when a 5% PVA solution was used. In contrast, the load of timolol was 2.3 µg per mg of spheres when the spheres were prepared using a 5% poly(ethylene-alt-maleic anhydride) (PEMA) solution.

Release of Timolol Maleate In Vitro

In 1.5 ml eppendorf tubes, 10 mg of timolol containing or blank microparticles were reconstituted with 1 ml of phosphate buffered saline (PBS). Samples were prepared in triplicate. The samples were incubated at 37° C. on a labquake rotating shaker (Barnstead/Thermolyne; Dubuque, Iowa, USA). At specific time points (1, 3, 5, and 8 hours; 1, 2, 3, 5, and 7 days; and once every 7 days thereafter until no pellets remained), the samples were centrifuged and the supernatant collected. 1 ml of PBS was added to the replace the withdrawn supernatant and the microparticles were resuspended and returned to the shaker. Supernatants for each of the sets of microspheres was frozen and stored at −80° C. for subsequent analysis using UV spectroscopy at 293 nm.

Figure 2A:
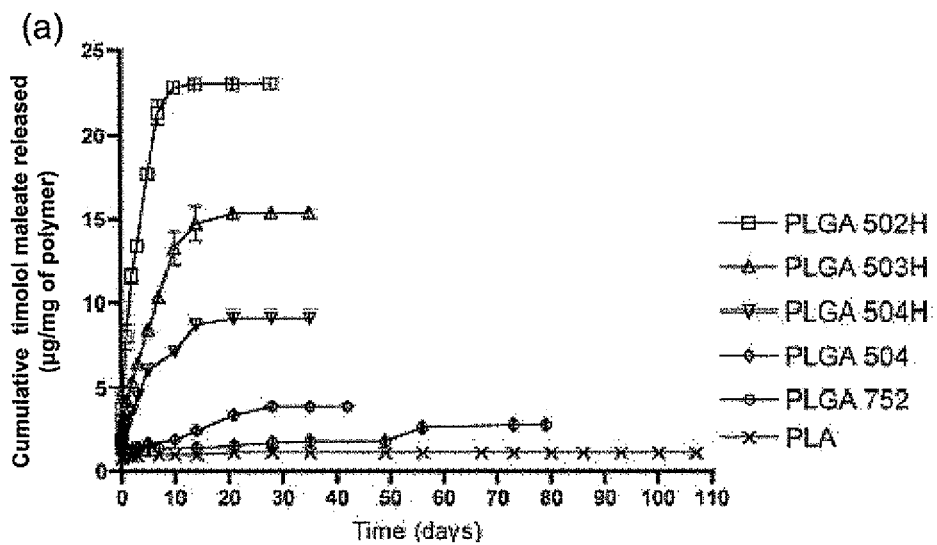
FIGS. 2*a* and 2*b* are line graphs showing the cumulative timolol maleate (20% w/w drug to polymer) released (μg of drug/mg of polymer) from polymeric microspheres over time (days).
Figure 2B:
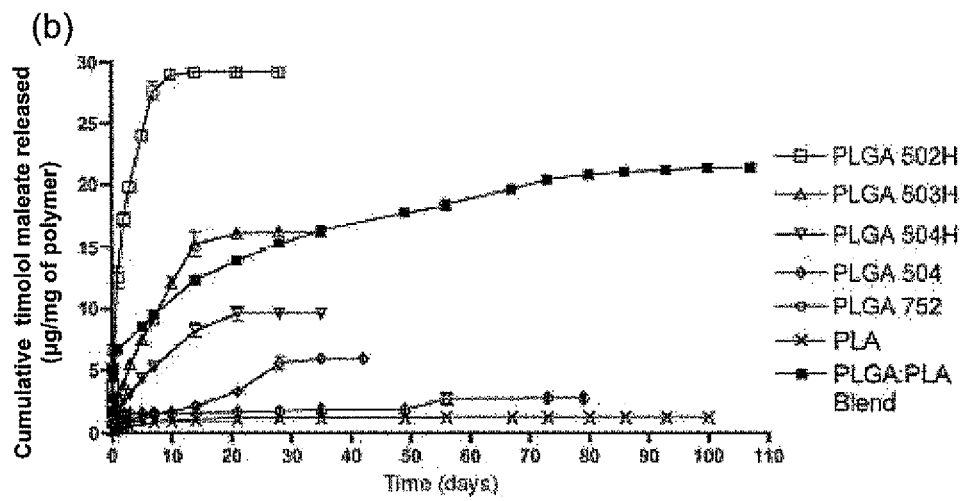

FIG. 2 shows the cumulative release profiles for various timolol maleate-loaded microparticles. The drug loading was 20% weight of timolol maleate to weight of polymer. The particles were stored in deionized water at 37° C. Following centrifugation at predetermined time points, the supernatant was extracted and timolol maleate content measured. FIG. 3 depicts the same values expressed as a percentage of the loading values in FIG. 1.

Figure 3A:
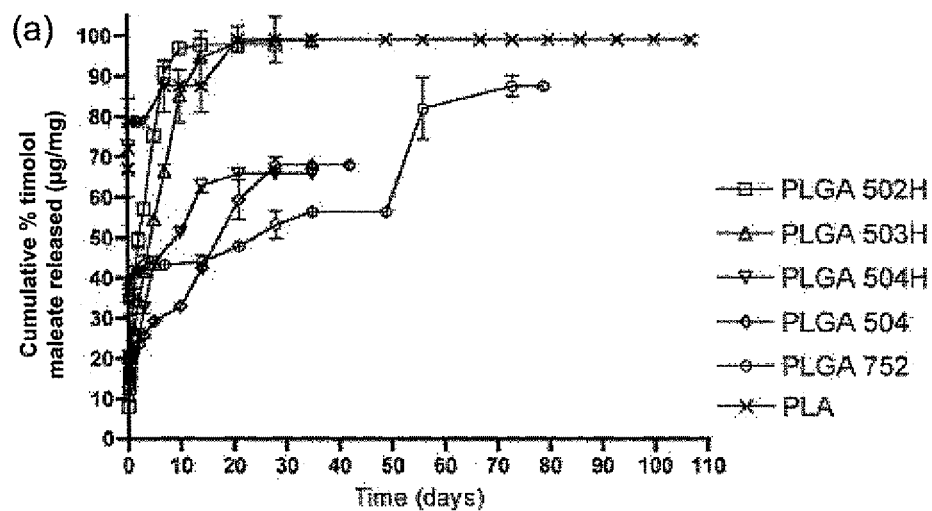
FIGS. 3*a* and 3*b* are line graphs showing the cumulative percentage of timolol maleate released from polymeric microspheres over time (days).
Figure 3B:
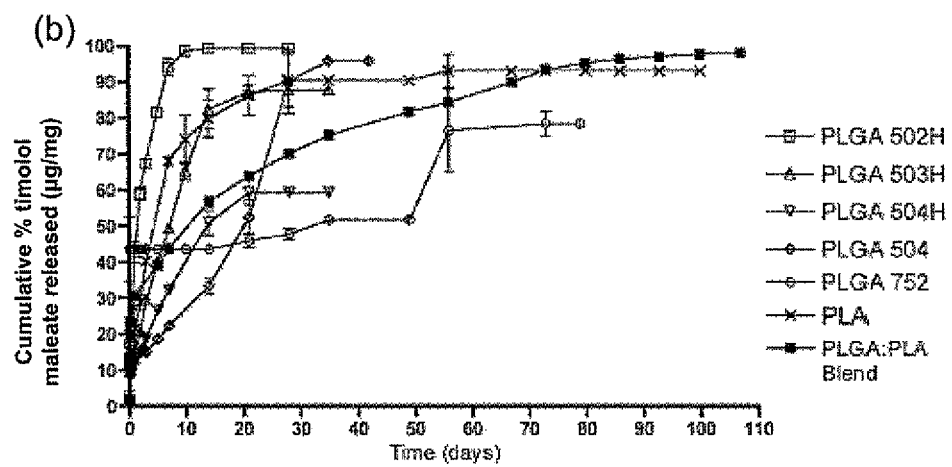

Excluding PLGA 752, it was observed that the length of timolol maleate release was directly proportional to the polymer molecular weight. While PLGA 502H had the greatest loading, it had the shortest release profile of approximately 10-15 days. PLGA 504 had the longest sustained release, approximately 35 days. Additionally, increasing the timolol maleate concentration from 10% to 20% induced a slight decrease in the rate of release, as shown in FIGS. 2 and 3. This trend is evident when comparing percent total cumulative release of PLGA 503H. As seen in FIGS. 3a and 3b, approximately 50% of the PLGA 503H microspheres' content is released between days 3 and 5 in the 10% loaded spheres. PLGA 503H, with 20% initial loading (FIG. 3), retained 50% of it timolol maleate content until day 7.

The cumulative release profile for PLGA 752 exhibited a substantial burst. Unlike other polymers whose release was approximately 10% over the first 3 hours, 43% of the timolol maleate was released from PLGA 752 in the first 3 hours. This burst was followed by a delay in release until day 38 and subsequent sustained delivery up to day 73 (see FIG. 3a), at which point no microspheres remained. The more hydrophobic polymers (PLGA 752 and PLA) exhibited substantial bursts at early time points (within the first day), followed by a small or delayed release over prolonged periods of time (56-73 days). The initial burst of timolol maleate released from PLGA 752 and PLA (see FIG. 3) can be attributed to the relative hydrophobicity of the polymers. Due to timolol maleate's hydrophilic nature, the drug's affinity for the hydrophilic polymers will be greater. Therefore, a lack of association with a more hydrophobic polymer (e.g., PLGA 752 or PLA) may lead to, when exposed to aqueous conditions, an increased leaching of the drug from the microspheres is observed. With respect to PLGA 752, the delayed release (38-73 days) correlates with a slower rate of microsphere degradation. This delayed rate if degradation is due to the polymer's relative hydrophobicity. This reasoning also supports the observation that while PLA microspheres were present for approximately 100 days, the release of timolol maleate lasted no longer than 56 days.

In an effort to combine the favorable loading of PLGA 502H and the longevity of PLA microspheres, the two polymers were blended during microsphere fabrication. The microspheres were prepared using the procedure described above. As shown in FIG. 3b, PLGA 502H:PLA blended microspheres released approximately 30% of the timolol maleate after 1 day. However, the remaining drug was released in a sustained manner over 107 days. Subconjunctival injection of 29% w/w loaded PLGA 502H:PLA blended microspheres would potentially deliver up to 163.5 µg of timolol maleate over a 107 day period.

In vitro release profiles of timolol maleate incorporated in microspheres prepared from various PLGA/PLA blends are shown in FIGS. 4a and 4b. FIG. 4a shows the in vitro release of timolol maleate from 502H/PLA (50-50), 503H/PLA (50-50), 504H/PLA (50-50), 504/PLA (50-50), and 502H/PLA (25-75) microspheres.

PLGA microspheres with carboxyl end groups had the shortest release profiles of 14-21 days. Previous studies found an accelerate degradation rate of PLGA devices due to polymer carboxyl end groups (Li et al., *J. Mat. Sci.-Mat. Med.*, 1, 131-139 (1990)) as seen with the shorter release profiles of PLGA 502H, 503H, and 504H. This carboxyl end group influence is noticeable when comparing the release of PLGA 504H and PLGA 504. Even with equivalent molecular weights, the release of timolol maleate from PLGA 504 is sustained 14 days longer than PLGA 504H, 35 and 21 days, respectively. The release of timolol maleate was found to correlate with the rates of polymer degradation. The lower molecular weight PLGA 502H has more carboxylic acid end groups and therefore a faster rate of degradation (see FIGS. 2 and 3).

Figure 5:
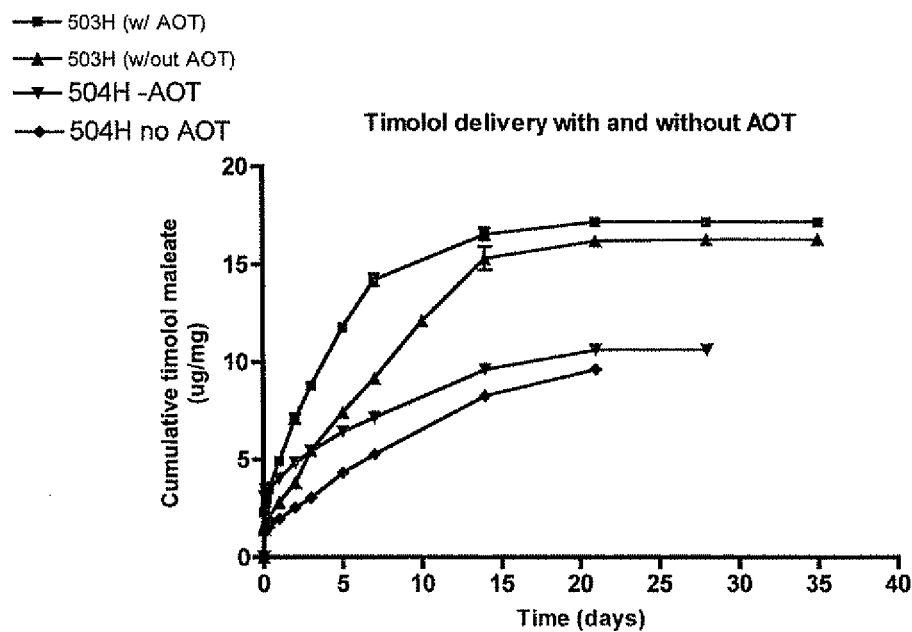
FIG. 5 is a graph showing the release of timolol maleate (μg of drug/mg of polymer) versus time (days) from: PLGA 503H with sodium dioctyl sulfosuccinate (AOT) (■) and without (▲); and PLGA 504 with AOT (▼) and without (♦).
Figure 6:
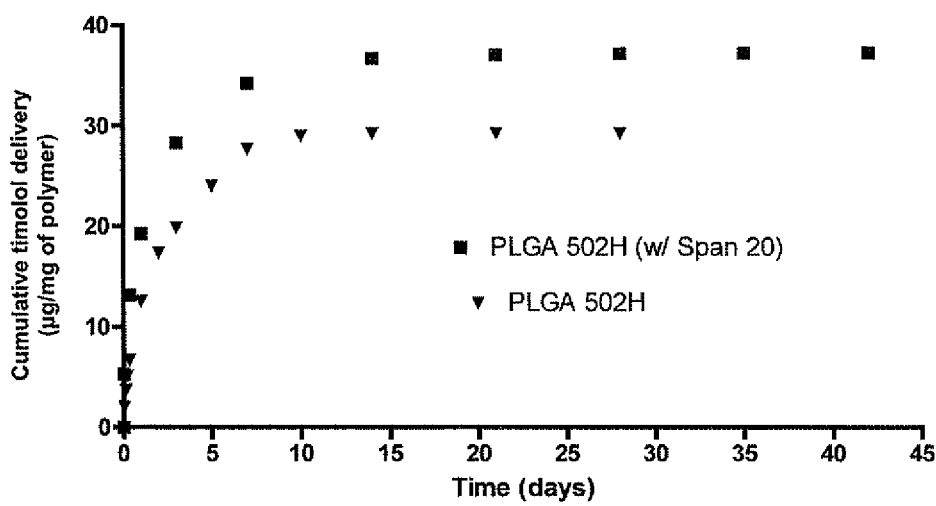
FIG. 6 is a graph showing the release of timolol maleate (μg of drug/mg of polymer) versus time (days) from: PLGA 502H with Span 20 (■) and without (▲).

In order to evaluate the criticality of the carboxylic acid groups to loading and release of timolol maleate, microspheres were prepared from PLGA 503H and 504H with and without sodium dioctyl sulfosuccinate (AOT), a negatively charged surfactant used to increase loading, particularly of positively charged drugs. A 20% w/w timolol maleate to PLGA microsphere formulation was prepared in the presence or absence of AOT. AOT was added at a concentration of 147 mM in the first step of the emulsion such that timolol maleate was suspended in water plus AOT. The results are shown in FIG. 5, The AOT had essentially no effect on loading or release of timolol maleate. Span 20 was used in place of AOT and again no significant effect on loading or release was observed. These results are shown in FIG. 6.

Figure 7:
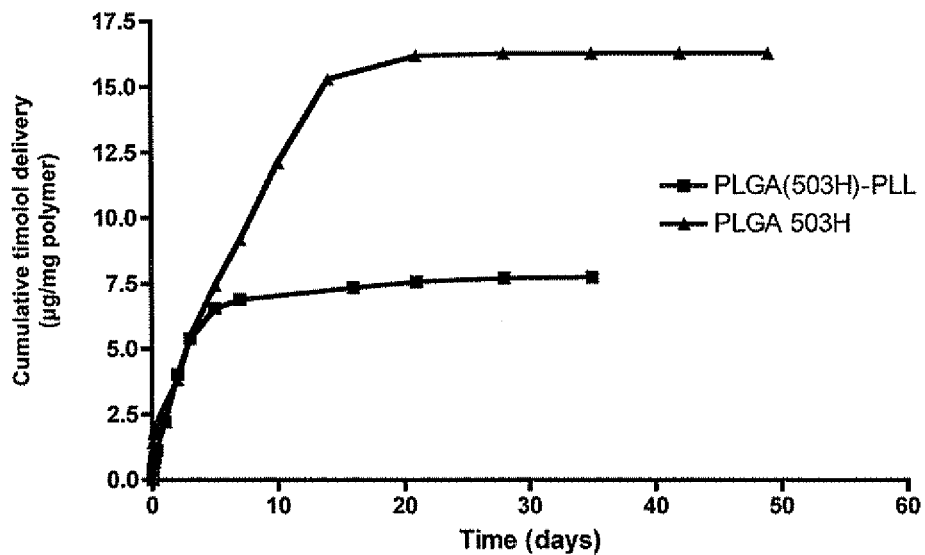
FIG. 7 is a graph showing the loading and release of timolol maleate (μg of drug/mg of polymer) versus time (days) for a block copolymer of PLGA 503H and polylysine (■) and PLGA 503H (▲).

Loading and release from a block copolymer of PLGA 503H and polylysine (PLL) was compared to PLGA 503H. The loading in the block copolymer was much less. Moreover, the duration of release from the block copolymer was approximately 15 days less than the duration of release from PLGA 503H. The results are shown in FIG. 7.

Particle Sizing and Scanning Electron Microscopy

The volume-weighted mean diameter of the microparticles from each batch was determined using a Beckman Coulter Multsizer 3 (Fullerton, Calif., USA) with a 100 µm diameter aperture based on a sample size of at least 80,000 microspheres.

Including all formulations, the average volume-weighted diameter of the microspheres was 15.9±3.2 m (mean±SD). Table 1 summarizes the average diameters for each polymer at 10% and 20% loading.

TABLE 1

| Microsphere Volume-Weighted Diameters | | | | |
|---|---|---|---|---|
| | 10% Loading | | 20% Loading | |
| | Timolol maleate (µm) | Blank (µm) | Timolol maleate (µm) | Blank (µm) |
| PLGA | | | | |
| 502H | 20.4 ± 5.3 | 15.2 ± 5.5 | 14.4 ± 5.4 | 14.0 ± 5.3 |
| 503H | 15.1 ± 6.5 | 19.7 ± 4.2 | 18.9 ± 4.3 | 17.0 ± 5.4 |
| 504H | 21.6 ± 3.2 | 14.00 ± 0.8 | 18.8 ± 5.3 | 12.1 ± 6.8 |
| 504 | 12.9 ± 5.9 | 18.2 ± 4.9 | 18.5 ± 7.4 | 11.4 ± 6.5 |
| 752 | 14.3 ± 5.2 | 15.2 ± 5.4 | 13.3 ± 4.6 | 17.6 ± 6.1 |
| PLA | 14.2 ± 4.4 | 15.1 ± 3.8 | 10.3 ± 5.0 | 11.9 ± 4.1 |
| 502H:PLA | | | 21.0 ± 11.5 | 19.2 ± 5.3 |

Scanning electron microscopy (SEM) analysis was used to examine the morphology of the spheres. Microspheres were sputter coated with gold for 30 seconds at 25 mA and SEM micrographs were taken on a FBI XL-30 environmental SEM operating at 4 kV.

Scanning electron microscopy (SEM) micrographs confirmed the results obtained from the Coulter multisizer. SEM of 20% timolol maleate loaded PLGA 503H showed relatively homogeneous spheres with minimal aggregation and smooth surfaces.

Example 2

In Vivo Studies of Pharmacokinetics and IOP Response of Timolol Maleate-Loaded Microspheres Lasered C57/BL6 mice and DBA/2J mice were used to investigate the effect of the in vivo release of timolol maleate on IOP and to quantify the concentration of timolol maleate in the aqueous humor over time. The lasered mouse model leads to elevated IOP for approximately 28 days following the lasering of the trabecular meshwork.

PLGA 502H/PLA timolol maleate-loaded microspheres were warmed to room temperature and resuspended in sterile PBS at a concentration of 25 mg/ml. The DBA/2J mice were anesthetized with isofluorane. 25 µl of the timolol-loaded or blank microspheres were injected subconjunctivally into the superotemporal quadrant of the right eye using a 30 gauge needle and a Hamilton syringe.

Figure 8:
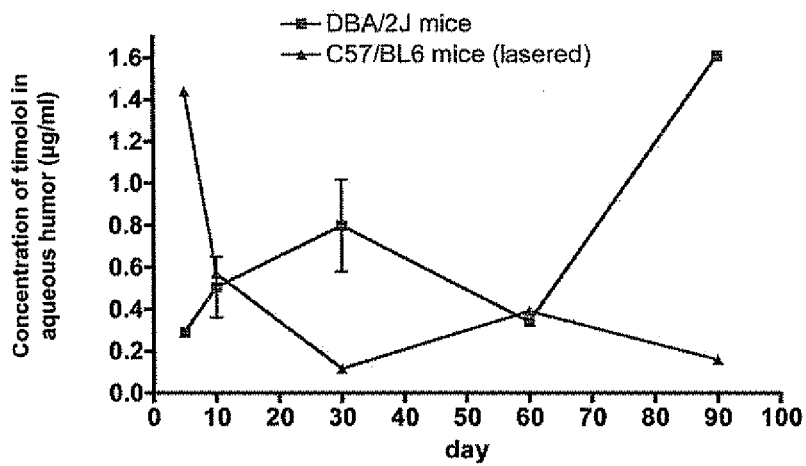
FIG. 8 is a graph showing the concentration of timolol maleate released in the aqueous humor (μg/mg) from PLGA 502H/PLA microspheres over time (days) in DBA/2.1 mice (■) and lasered C57/BL6 mice (●).

The eyes were nucleated and the aqueous humor was collected using a 30 G butterfly needle, Timolol maleate was quantified using HPLC with an LC-18 column (INtersil ODS-3) at 294 nm. The results are shown in FIG. 8. The concentration of timolol maleate in the aqueous humor is within the therapeutic window needed for IOP reduction in humans over the 90 day period measured.

IOP was measured using a rebound tonometer specifically designed to be used with rodents (Tonolab®). Following sedation by isofluorane anesthesia and 10 minutes after the loss of the eye lid reflex, ten measurements were taken at the same time of day to avoid diurnal TOP changes. The PLGA 502H/PLA timolol spheres showed an IOP response that is statistically identical to 0.5% timolol drops over all the time periods measured.

Example 3

Preparation and In Vitro Release Studies of Microspheres Containing Ofloxacin

Microspheres containing ofloxacin were prepared using the polymers described in Example 1. The microspheres were prepared using the phrase separation single emulsion solvent evaporation technique similar to the method described in Example 1. The in vitro release studies were conducted as described in Example 1.

Analysis using UV spectroscopy was done at 288 nm for ofloxacin. Concentration of dissolved ofloxacin was determined as a function of time from their respective standard curves. Plotting ofloxacin concentration versus UV absorbance produced a calibration curve for quantification of ofloxacin. A linear fit was established from ~0.09-25 µg/mL of ofloxacin (Y=15.196x+0.0571; $r^2$=0.9999) in phosphate buffered saline.

Figure 9A:
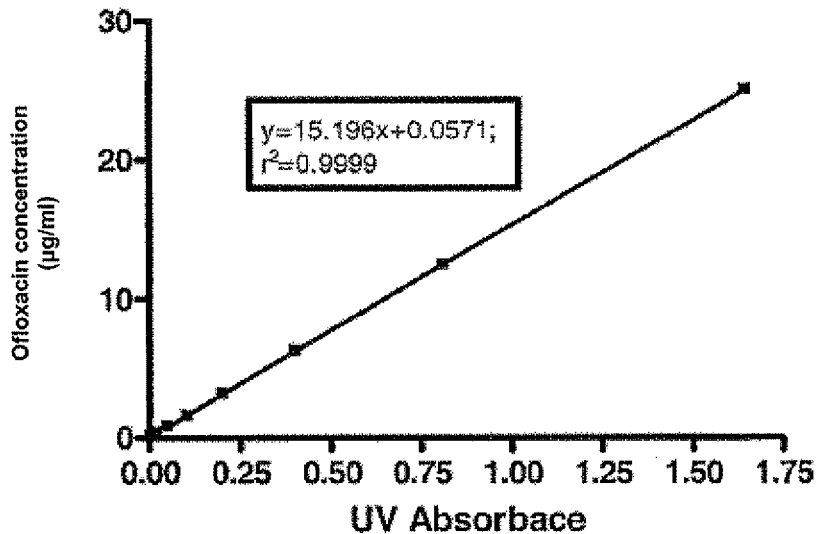
FIGS. 9a is a graph showing the concentration curve of ofloxacin (μg/mL) versus UV absorbance (nm).
Figure 9B:
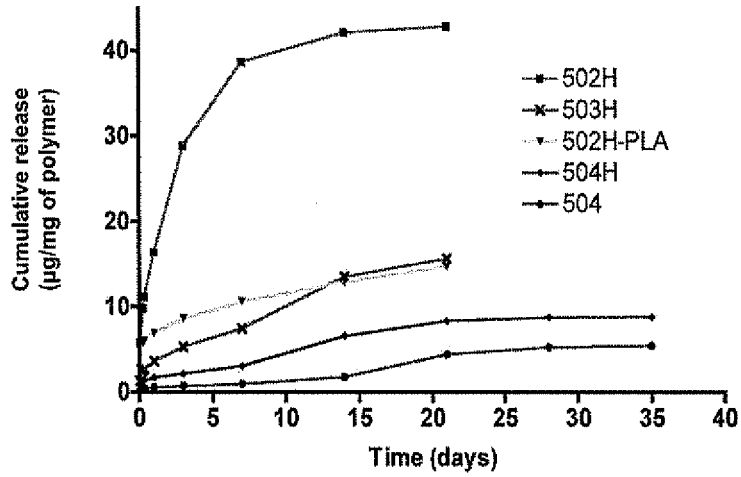
FIG. 9b is a graph showing the cumulative ofloxacin release (μg/mg of polymer) versus time (days) from microspheres prepared from PLGA 502H (■), PLGA 503H (x); PLGA 502H -PLA (▼), PLGA 504H (♦), and PLGA 504 (●).

The in vitro release profile for ofloxacin is shown in FIG. 9. FIG. 9a shows the standard curve for ofloxacin and FIG. 9b shows the cumulative release profiles for ofloxacin-loaded microspheres prepared from different polymers. PLGA 502H had the shortest release profile of approximately 14 days. PLGA 503H, 504H, and 504 microspheres each released ofloxacin for a period of approximately 25-28 days. PLGA 502H-PLA blend microspheres released ofloxacin for approximately 49 days.

Example 4

Figure 10:
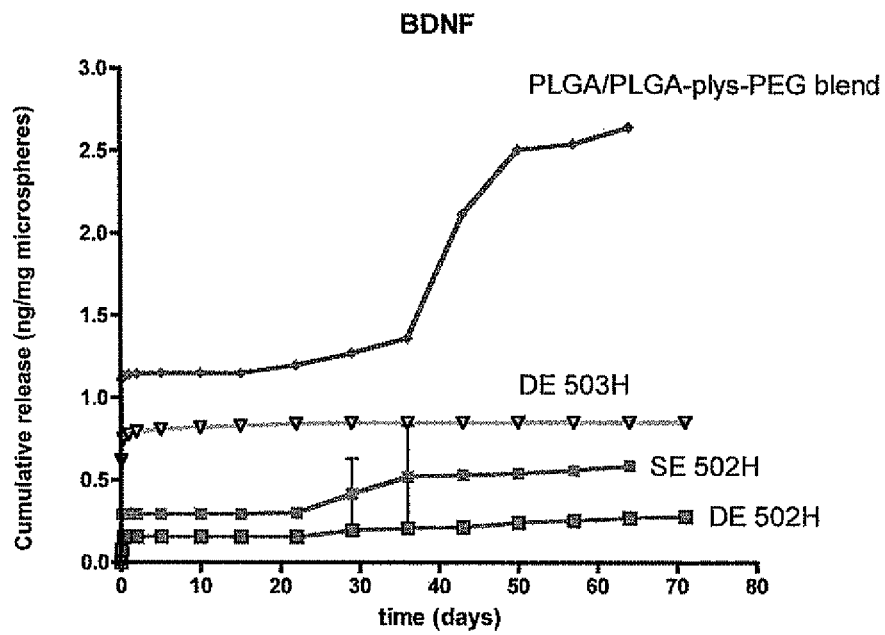
FIG. 10 is a graph showing the cumulative release of brain-derived neurotrophic factor (BDNF) (ng of drug/mg microspheres) versus time (days) from: PLGA 502H microspheres prepared by a single emulsion process (■) and double emulsion process (□); PLGA 503H microspheres prepared by a double emulsion process (∇); and microspheres prepared from a blend of PLGA 502H and PLGA 503H-polylysine-polyethylene glycol graft copolymer (♦).

Preparation and in Vitro Release Studies of Brain Derived Neurotrophic Factor (BDNF)-Loaded Microspheres Brain-derived neurotrophic factor (BDNF) was loaded into the following: PLGA 502H microspheres prepared using the single emulsion (SE) or double emulsion (DE) procedures described above; PLGA 503H prepared from the double emulsion (DE) procedure; and microspheres prepared from a blend of PLGA 502H and PLGA 503H-polylysine-polyethylene glycol graft copolymer, wherein the polylysine has a molecular weight of about 1000 kDa and the polyethylene glycol has a molecular weight of approximately 1500. In the graft copolymer, there were approximately 4 polyethylene glycol molecules per PLGA chain in the graft copolymer. The microspheres prepared from the blend were prepared using the SE process. The results are shown in FIG. 10. The loading of BDNF was highest for the microspheres prepared from the blend; however, the duration of release for the blend approximately 5 days shorter than the PLGA 502H and 503H microspheres prepared by the DE technique. Loading was lowest for the microspheres prepared from PLGA 502H using the DE technique.

Figure 11:
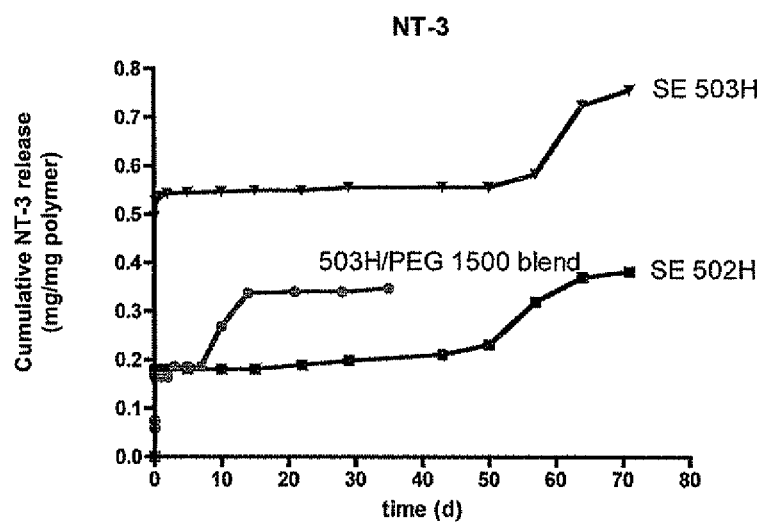
FIG. 11 is a graph showing the cumulative release of NT-3 (mg of drug/mg of polymer) as a function of time (days) from: PLGA 503H microspheres prepared by a single emulsion method (▼); PLGA 502H microspheres prepared by a single emulsion method (■); and microspheres prepared from a blend of PLGA 503H and polyethylene glycol 1500 (●).

In vitro release studies were also done on NT-3-loaded microspheres prepared from PLGA 503H and 502H prepared using the SE technique as well as a PLGA 503H/PEG 1500 blend. NT-3 is structurally identical to BDNF but has a number of different amino acids in its sequence. The results are shown in FIG. 11. Loading varied based on the polymer chosen. The addition of PEG 1500 altered the release profile, which were substantially similar for PLGA 502H and 503H.

We claim:

1. A biodegradable polymeric microparticulate pharmaceutical composition for delivery of one or more water-soluble active agents,
    wherein the biodegradable polymeric microparticles comprise a biodegradable polymer and between one and 50 weight percent of the water-soluble active agent dispersed therein,
    wherein the hydrophilicity of the polymer forming the microparticles corresponds to the hydrophilicity of the active agent to be released, the hydrophilicity and charge of the polymer are selected to optimize percent loading of the active agent, and the molecular weight and monomer composition result in release of an effective amount of the active agent over a period of time of at least 60 days, when administered subconjunctivally, equivalent to administration of the active agent via the same route of administration in the absence of microparticles.

2. The composition of claim 1, wherein the microparticles are formed from one or more polymers selected from the group consisting of poly(lactic-co-glycolic) acid (PLGA)and a blend of PLGA and polylactic acid (PLA).

3. The composition of claim 1, wherein the one or more water-soluble active agents are selected from the group consisting of selective or non-selective beta-adrenergic receptor blockers that lower intraocular pressure, antibiotics, steroids, growth factors, chemotherapeutic agents, and combinations thereof.

4. The composition of claim 3, wherein the selective or non-selective beta-adrenergic receptor blockers that lower intraocular pressure is selected from the group consisting of timolol, betaxolol, levobunolol, carteolol, metipranolol, and combinations thereof.

5. The composition of claim 3, wherein the antibiotic is selected from the group consisting of fluoroquinolone antibiotics, such as ofloxacin, levofloxacin, moxifloxacin, and gatifloxacin; aminoglycosides, such as streptomycin, kanamycin, aminodeoxykanamycin, kasugamycin, gentamicin, neomycin, tobramycin, netilmicin, and paromomycin; diaminopyrimidines, such as trimethoprim, and combinations thereof.

6. The composition of claim 3, wherein the growth factor is selected from the group consisting of NT-4, NT-3, brain derived neurotrophic factor (BDNF), and combinations thereof.

7. The composition of claim 3, wherein the steroid is selected from the group consisting of dexamethasone, hydroxydione, minaxolone, ORG 20599, ORG 21465, and combinations thereof.

8. The composition of claim 4, wherein the one or more active agents is timolol or a pharmaceutically acceptable salt thereof.

9. The composition of claim 1, wherein the percent loading of active agent is between 5 and 30 weight percent.

10. The composition of claim 1, wherein the polymer is PLGA having a molecular weight in the range from about 10 kD to about 80 kD.

11. The composition of claim 1 wherein the period of release is 90 days or greater in vivo.

12. The composition of claim 1 wherein the polymer comprises a plurality of carboxyl groups.

13. The composition of claim 12 wherein the polymer is PLGA.

14. The composition of claim 1, wherein the composition further comprises one or more pharmaceutically acceptable excipients.

15. A method for administering one or more water-soluble active agents, comprising administering to the eye a biodegradable microparticulate pharmaceutical composition for delivery of the water-soluble active agent,
wherein the biodegradable polymeric microparticles comprise a biodegradable polymer and between one and 50 weight percent of the water-soluble active agent dispersed therein,
wherein the hydrophilicity of the polymer forming the microparticles corresponds to the hydrophilicity of the active agent to be released, the hydrophilicity and charge of the polymer are selected to optimize percent loading of the active agent, and the molecular weight and monomer composition result in release of an effective amount of the active agent over a period of time of at least 60 days, when administered subconjunctivally, equivalent to administration of the active agent via the same route of administration in the absence of microparticles.

16. The method of claim 15, comprising administering the microparticles to the eye subconjunctivally.

17. The method of claim 15, wherein the microparticles are formed from poly(lactic-co-glycolic) acid (PLGA) or a blend of PLGA and polylactic acid (PLA).

18. The method of claim 15, wherein the one or more water-soluble active agents are selected from the group consisting of selective or non-selective beta-adrenergic receptor blockers that lower intraocular pressure, antibiotics, steroids, growth factors, chemotherapeutic agents, and combinations thereof.

19. The method of claim 18, wherein the selective or non-selective beta-adrenergic receptor blocker that lowers intraocular pressures is selected from the group consisting of timolol, betaxolol, levobunolol, carteolol, metipranolol, and combinations thereof.

20. The method of claim 18, wherein the antibiotic is selected from the group consisting of fluoroquinolone antibiotics, such as ofloxacin, levofloxacin, moxifloxacin, and gatifloxacin; aminoglycosides, such as streptomycin, kanamycin, aminodeoxykanamycin, kasugamycin, gentamicin, neomycin, tobramycin, netilmicin, and paromomycin; diaminopyrimidines, such as trimethoprim, and combinations thereof.

21. The method of claim 18, wherein the growth factor is selected from the group consisting of NT-4, NT-3, brain derived neurotrophic factor (BDNF), and combinations thereof.

22. The method of claim 18, wherein the steroid is selected from the group consisting of dexamethasone, hydroxydione, minaxolone, ORG 20599, ORG 21465, and combinations thereof.

23. The method of claim 19, wherein the one or more active agents is timolol or a pharmaceutically acceptable salt thereof.

24. The method of claim 15, wherein the polymer is carboxylated PLGA and the percent loading of drug is from 5 to 30% by weight.

25. The method of claim 24, wherein the polymer is a PLGA with a molecular weight from about 10 kD to about 80 kD.

26. The method of claim 15, comprising administering the composition by injection.

27. The method of claim 26, comprising administering the composition subconjunctivally.

28. A kit comprising the compositions of claim 1.

29. The kit of claim 28, wherein the kit further comprises instructions for preparing and/or administering the composition, optionally comprising a needle and syringe for administering the composition.

30. The kit of claim 28, wherein the microparticles and the carrier are stored in the same container or in separate containers.

31. The kit of claim 30, wherein the container is selected from the group consisting of sterile vials, jars, sealed ampules, and combinations thereof.

* * * * *

UNITED STATES PATENT AND TRADEMARK OFFICE
CERTIFICATE OF CORRECTION

PATENT NO. : 8,492,334 B2  
APPLICATION NO. : 12/664792  
DATED : July 23, 2013  
INVENTOR(S) : Erin Lavik et al.

Page 1 of 1

It is certified that error appears in the above-identified patent and that said Letters Patent is hereby corrected as shown below:

In the Claims:

Claim 15, column 27, line 10, replace "microparticulate pharmaceutical composition" with --polymeric microparticulate pharmaceutical composition--.
Claim 24, column 28, line 20, replace "drug" with --active agent--.
Claim 28, column 28, line 29, replace "compositions" with --composition--.
Claim 30, column 28, lines 34-35, replace "and the carrier" with --and a carrier--.

Signed and Sealed this  
Twenty-second Day of October, 2013

Teresa Stanek Rea  
*Deputy Director of the United States Patent and Trademark Office*

UNITED STATES PATENT AND TRADEMARK OFFICE
CERTIFICATE OF CORRECTION

PATENT NO. : 8,492,334 B2 Page 1 of 1
APPLICATION NO. : 12/664792
DATED : July 23, 2013
INVENTOR(S) : Lavik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 618 days.

Signed and Sealed this
Eighth Day of September, 2015

Michelle K. Lee
*Director of the United States Patent and Trademark Office*